(12) United States Patent
Nichols et al.

(10) Patent No.: US 10,485,587 B2
(45) Date of Patent: Nov. 26, 2019

(54) LOW PROFILE CONNECTORS

(71) Applicant: GLOBUS MEDICAL, INC., Audubon, PA (US)

(72) Inventors: Jeff Nichols, Philadelphia, PA (US); Khiem Pham, Chalfont, PA (US)

(73) Assignee: GLOBUS MEDICAL, INC, Audubon, PA (US)

( * ) Notice: Subject to any disclaimer, the term of this patent is extended or adjusted under 35 U.S.C. 154(b) by 59 days.

(21) Appl. No.: 15/253,941

(22) Filed: Sep. 1, 2016

(65) Prior Publication Data

US 2016/0367292 A1 Dec. 22, 2016

Related U.S. Application Data

(63) Continuation-in-part of application No. 14/882,512, filed on Oct. 14, 2015, which is a continuation-in-part of application No. 14/725,406, filed on May 29, 2015, which is a continuation of application No. 13/669,527, filed on Nov. 6, 2012, now Pat. No. 9,072,547.

(51) Int. Cl.
*A61B 17/70* (2006.01)
*A61B 17/80* (2006.01)

(52) U.S. Cl.
CPC ...... *A61B 17/7052* (2013.01); *A61B 17/7023* (2013.01); *A61B 17/7034* (2013.01); *A61B 17/7041* (2013.01); *A61B 17/7055* (2013.01); *A61B 17/809* (2013.01)

(58) Field of Classification Search
CPC ............ A61B 17/7007; A61B 17/7008; A61B 17/7041; A61B 17/7043; A61B 17/7049; A61B 17/705; A61B 17/7052; A61B 17/7001; A61B 17/7014; A61B 17/7032; A61B 17/7034; A61B 17/7035; A61B 17/7037; A61B 17/7038; A61B 17/704; A61B 17/7046; A61B 17/8685
See application file for complete search history.

(56) References Cited

U.S. PATENT DOCUMENTS

| | | | |
|---|---|---|---|
| 5,501,684 A * | 3/1996 | Schlapfer | A61B 17/60 403/90 |
| 6,063,090 A * | 5/2000 | Schlapfer | A61B 17/7037 606/270 |
| 6,074,391 A * | 6/2000 | Metz-Stavenhagen | A61B 17/7032 606/278 |

(Continued)

*Primary Examiner* — Lynnsy M Summitt

(57) ABSTRACT

Modular devices, assemblies, and methods for coupling one or more fixation elements, such as bone fasteners and/or elongate rods. The device includes at least one coupling element having a body portion for receiving a bone fastener and an extension portion extending transversely from the body portion. A locking assembly is received in the coupling element and includes a locking member, a clamp portion, and a ring portion, wherein the locking member is configured to contact an upper portion of the clamp portion and the ring portion is configured to at least partially surround a lower portion of the clamp portion. When unlocked, the bone fastener is moveable within the clamp portion to allow for polyaxial movement of bone fastener relative to the coupling element, and when locked, the bone fastener is fixed relative to the coupling element.

19 Claims, 14 Drawing Sheets

(56) References Cited

U.S. PATENT DOCUMENTS

| | | | | |
|---|---|---|---|---|
| 7,186,255 B2* | 3/2007 | Baynham | A61B 17/7035 | 606/266 |
| 7,837,714 B2* | 11/2010 | Drewry | A61B 17/7052 | 606/250 |
| 8,029,546 B2* | 10/2011 | Capote | A61B 17/7037 | 606/257 |
| 8,252,030 B2* | 8/2012 | Iott | A61B 17/7041 | 606/264 |
| 8,308,782 B2* | 11/2012 | Jackson | A61B 17/7008 | 606/305 |
| 8,475,495 B2* | 7/2013 | Iott | A61B 17/7032 | 606/246 |
| 8,585,741 B2* | 11/2013 | Gabelberger | A61B 17/7035 | 606/264 |
| 8,672,978 B2* | 3/2014 | Dant | A61B 17/7032 | 606/250 |
| 8,951,290 B2* | 2/2015 | Hammer | A61B 17/7034 | 606/267 |
| 8,951,294 B2* | 2/2015 | Gennari | A61B 17/7076 | 606/266 |
| 8,979,898 B2* | 3/2015 | Ark | A61B 17/7037 | 606/249 |
| 9,044,273 B2* | 6/2015 | Richelsoph | A61B 17/7001 | |
| 9,198,695 B2* | 12/2015 | Shluzas | A61B 17/7032 | |
| 9,271,761 B2* | 3/2016 | Legallois | A61B 17/704 | |
| 9,320,546 B2* | 4/2016 | Keyer | A61B 17/7007 | |
| 2004/0147928 A1* | 7/2004 | Landry | A61B 17/1671 | 606/86 A |
| 2007/0135817 A1* | 6/2007 | Ensign | A61B 17/7007 | 606/96 |
| 2007/0288004 A1* | 12/2007 | Alvarez | A61B 17/7032 | 606/86 A |
| 2008/0306538 A1 | 12/2008 | Moore et al. | | |
| 2009/0118765 A1 | 5/2009 | Mueller et al. | | |
| 2010/0087867 A1* | 4/2010 | Klein | A61B 17/7007 | 606/278 |
| 2010/0094349 A1* | 4/2010 | Hammer | A61B 17/7034 | 606/264 |
| 2010/0234893 A1* | 9/2010 | Iott | A61B 17/7035 | 606/278 |
| 2010/0268279 A1* | 10/2010 | Gabelberger | A61B 17/7035 | 606/278 |
| 2011/0040335 A1* | 2/2011 | Stihl | A61B 17/7032 | 606/302 |
| 2012/0035659 A1 | 2/2012 | Barrus et al. | | |
| 2012/0059426 A1* | 3/2012 | Jackson | A61B 17/7008 | 606/300 |
| 2012/0130436 A1* | 5/2012 | Haskins | A61B 17/7032 | 606/305 |
| 2012/0203278 A1 | 8/2012 | Gil et al. | | |
| 2012/0253397 A1 | 10/2012 | Kraus | | |
| 2014/0316468 A1* | 10/2014 | Keiser | A61B 17/7052 | 606/252 |
| 2015/0100089 A1* | 4/2015 | Richelsoph | A61B 17/7001 | 606/246 |
| 2015/0257792 A1* | 9/2015 | Jackson | A61B 17/7037 | 606/266 |

* cited by examiner

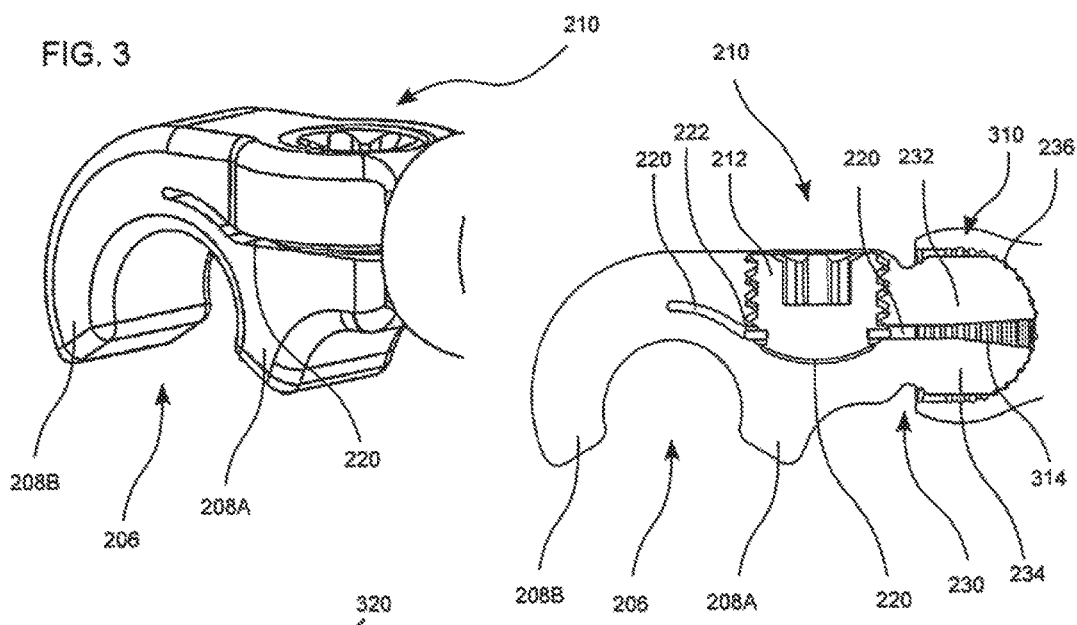
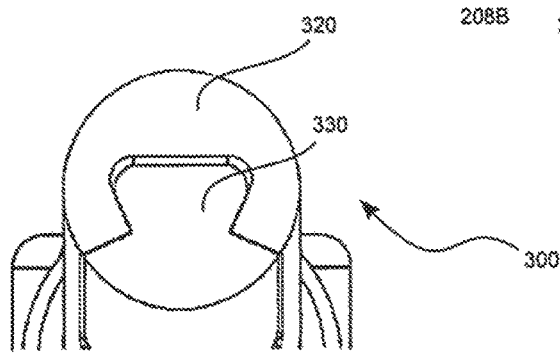
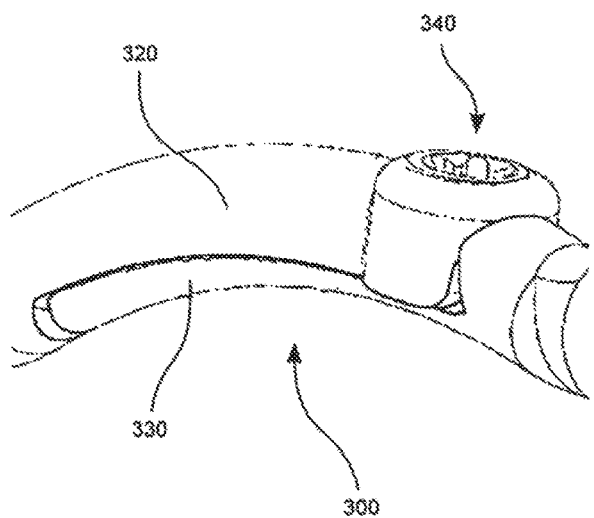

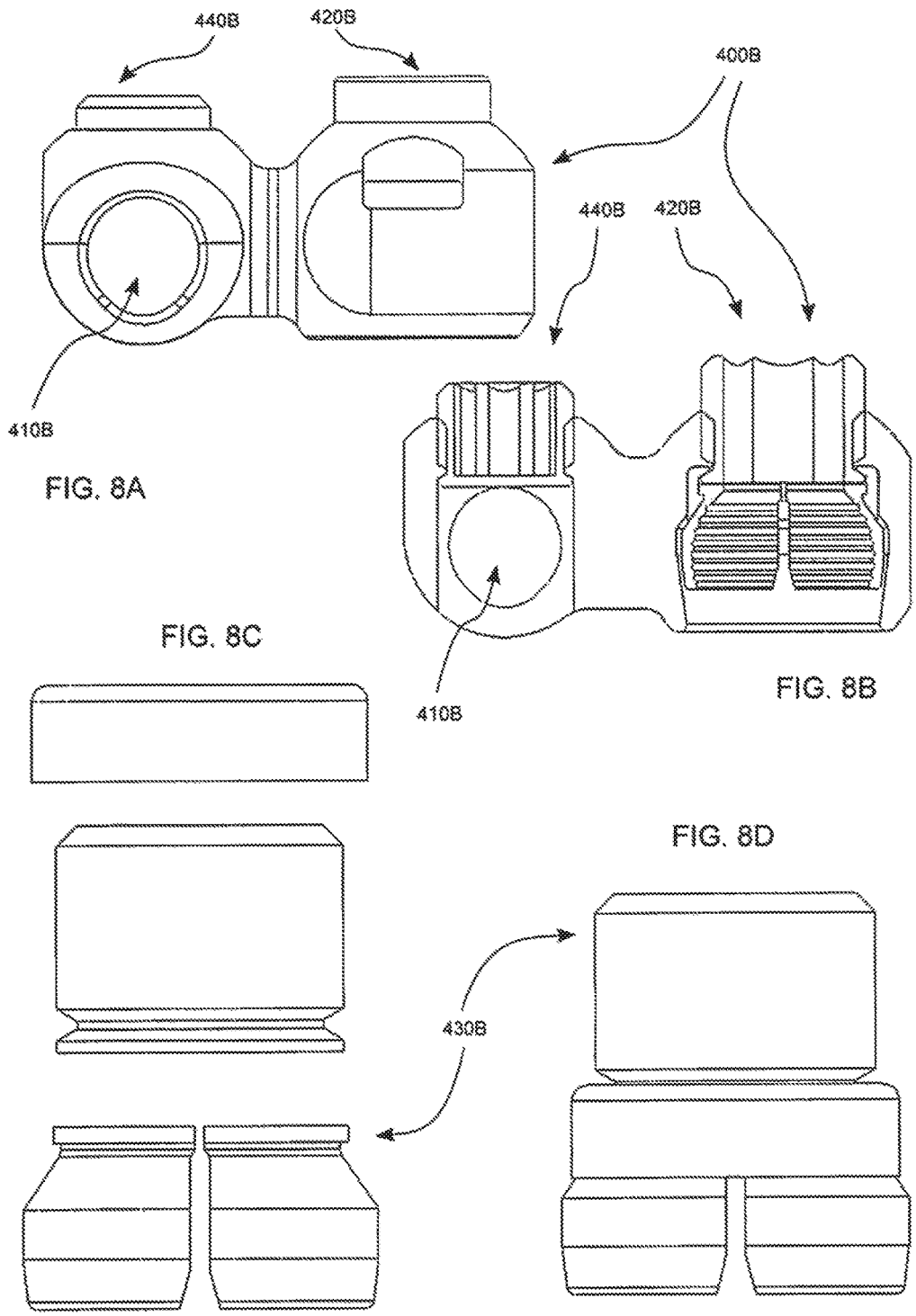

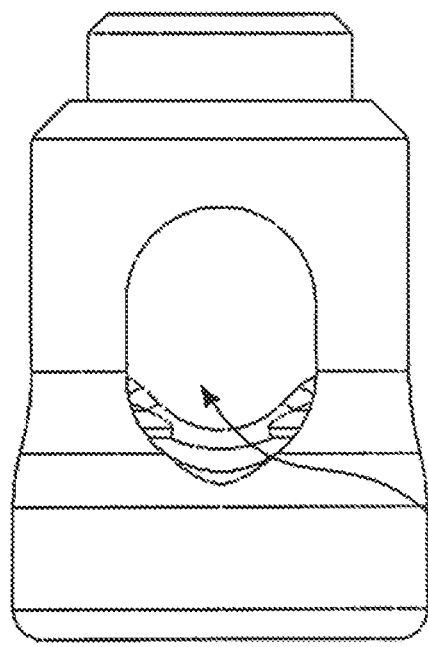
FIG. 10A
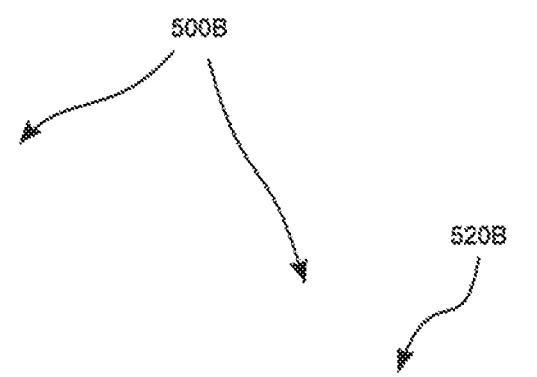
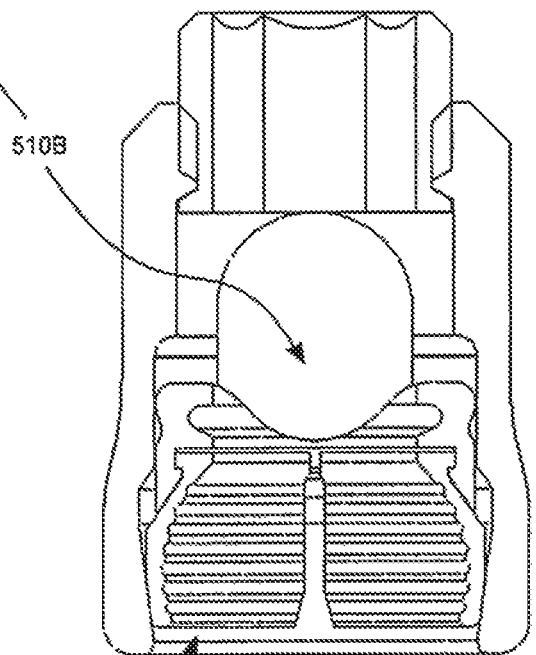
FIG. 10B

FIG. 11A
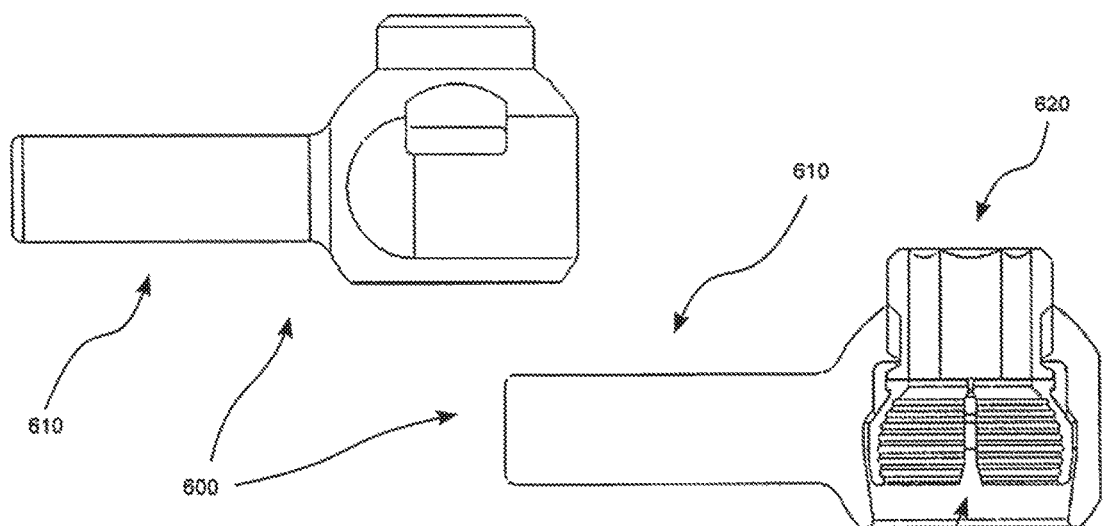
FIG. 11B
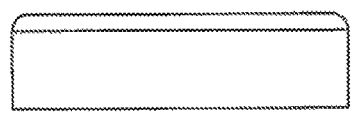
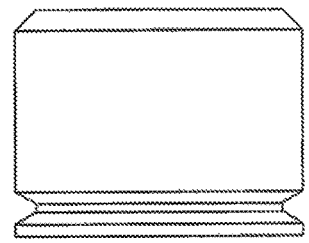
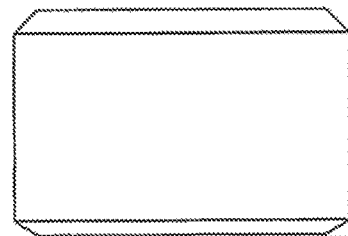
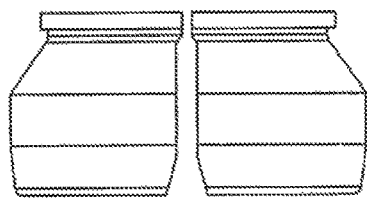
FIG. 11C
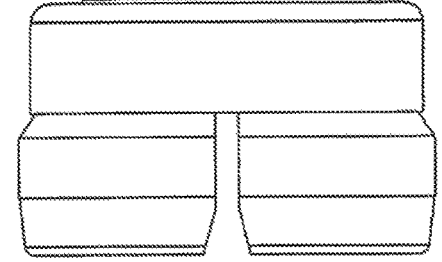
FIG. 11D

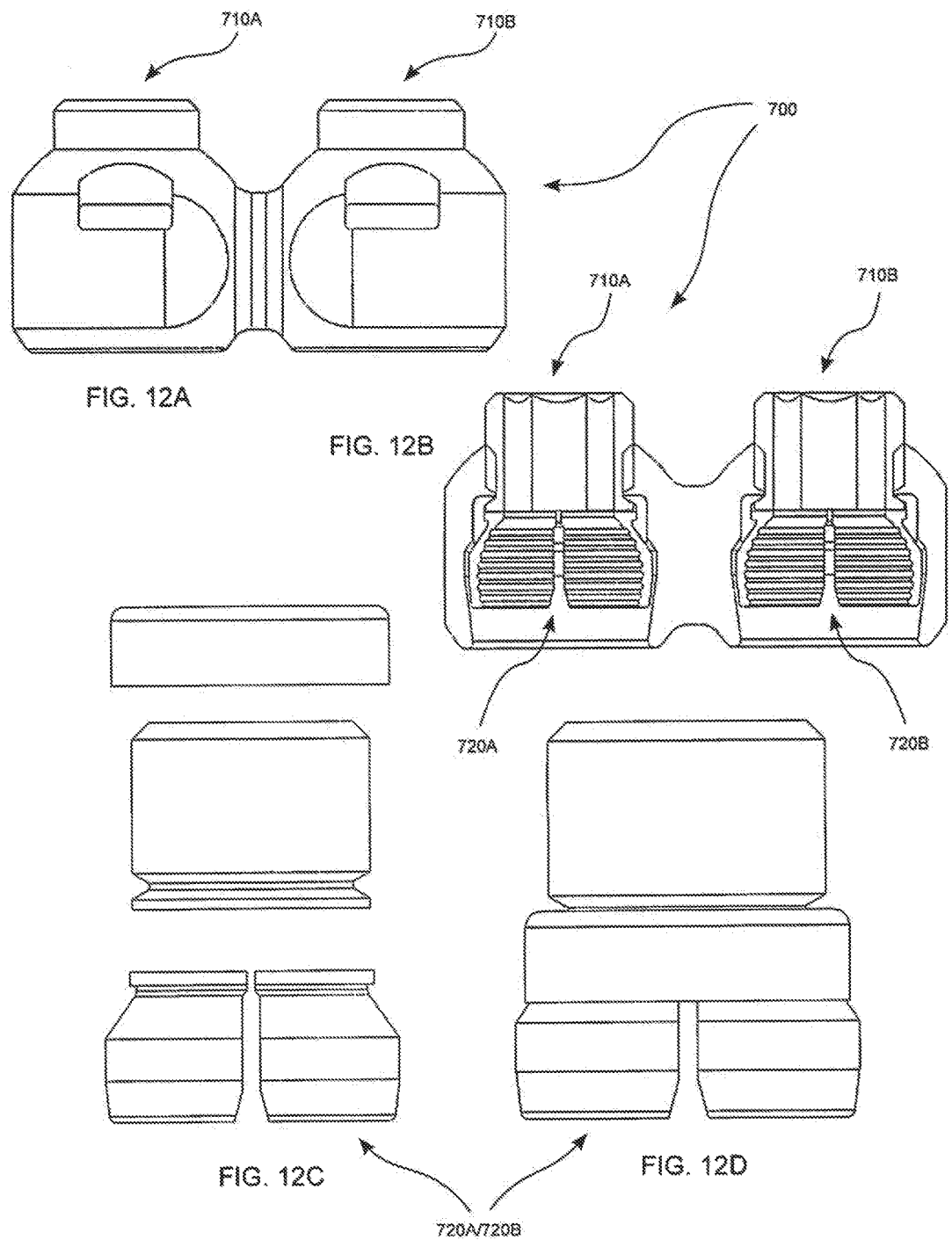

LOW PROFILE CONNECTORS

CROSS REFERENCE TO RELATED APPLICATION

This application is a continuation-in-part of U.S. application Ser. No. 14/882,512, filed Oct. 14, 2015, which is a continuation-in-part of U.S. application Ser. No. 14/725,406, filed May 29, 2015, which is a continuation of U.S. application Ser. No. 13/669,527, filed Nov. 6, 2012, now U.S. Pat. No. 9,072,547, which are hereby incorporated by reference in their entireties for all purposes.

FIELD OF THE INVENTION

The invention relates to connectors for fixation elements, including interconnecting at least two spinal fixation rods or interconnecting at least two adjacent vertebrae.

BACKGROUND OF THE INVENTION

Bones and bony structures are susceptible to a variety of weaknesses that can affect their ability to provide support and structure. Weaknesses and deformities in bony structures have numerous potential causes, including degenerative diseases, tumors, fractures, and dislocations. Advances in medicine and engineering have provided health care practitioners with a number of devices and techniques for alleviating or curing those weaknesses.

With respect to the spinal column, additional support may be necessary to address such weaknesses and deformities. Surgical techniques for stabilizing the spinal column, such as spinal fusion, have been developed to eliminate pain and other detrimental effects associated with spinal column defects. The placement of one or more screws, rods, plates, or cages may be required in association with some spinal stabilization techniques.

The strength and stability of a dual rod, plate, or other elongate member assembly can be increased by coupling the two rods with a cross connector which extends substantially horizontal to the longitudinal axes of the rods across the spine. Due to a wide variety of factors, the two rods are rarely geometrically aligned in clinical situations. A cross connector with at least some adjustability can be provided to accommodate for variations from geometrical alignment.

SUMMARY OF THE INVENTION

The invention relates to devices for coupling first and second elongate spinal fixation elements and for coupling first and second vertebrae. According to one embodiment, the device includes a first connector member having proximal and distal portions, the distal portion including an engagement portion configured and dimensioned to provisionally receive the first elongate spinal fixation element with an interference fit; a translation member having proximal and distal portions the proximal portion of the first connector member operatively associated with the proximal portion of the translation member to provide polyaxial movement of the first connector member relative to the translation member; a second connector member having proximal and distal portions, the distal portion configured and dimensioned to receive the second elongate spinal fixation element and the proximal portion coupled to the translation member; and a first locking member to secure the first elongate spinal fixation element in the engagement portion of the first connector member and to lock the polyaxial movement, fixing the first connector member relative to the first translation member.

In additional embodiments in accordance with the disclosure, the proximal portion of the first connector member includes a sphere and the distal portion of the translation member includes a bore for receiving the sphere to provide the polyaxial movement. A surface of the bore and a surface of the sphere may further include grooves and the other of the surface of the bore and the surface of the sphere includes ridges.

Another embodiment of the device features the engagement portion of the first connector including proximal and distal arms, at least one of the proximal and distal arms resiliently flexing open to accept the first elongate spinal fixation element and flexing back to provisionally receive the first elongate spinal fixation element with the interference fit. The first connector member may also include a slit extending between the proximal portion of the first connector member to the distal portion of the first connector member, the slit allowing the resilient flexing of the at least one of the proximal and distal arms of the engagement portion of the first connector. The first locking member may additionally include a first set screw and a hole on the first connector member and operatively associated with the slit such that threading of the first set screw into the hole moves the proximal and distal arms relative to one another to secure the first elongate spinal fixation element in the engagement portion of the first connector member. Furthermore, the slit may divide the sphere into first and second portions and wherein threading of the first set screw into the hole splays the first and second portions of the sphere to lock the polyaxial movement, fixing the first connector member relative to the translation member. The translation member may additionally include first and second translation elements, the first translation element including the proximal portion of the translation member and the second translation element including the distal portion of the translation member; and wherein the first and second translation elements are moveable relatively to each other to adjust a distance between the first and second connector members. In some embodiments the first and second translation elements move relative to each other with translation movement, substantially free of rotation. The first and second translation elements may be coupled with a dove-tail connection. The first and second translation elements may further move relative to each other along an arced path.

In another embodiment in accordance with the disclosure, a device for coupling first and second elongate spinal fixation elements includes a first connector member having proximal and distal portions, the distal portion including an engagement portion configured and dimensioned to provisionally receive the first elongate spinal fixation element with an interference fit; a second connector member having proximal and distal portions, the distal portion including an engagement portion configured and dimensioned to provisionally receive the second elongate spinal fixation element with an interference fit; a translation member having first and second portions, the proximal portion of the first connector member operatively associated with the first portion of the translation member to provide polyaxial movement of the first connector member relative to the translation member, the proximal portion of the second connector member operatively associated with the second portion of the translation member to provide polyaxial movement of the second connector member relative to the translation member; a first locking member to secure the first elongate spinal fixation element in the engagement portion of the first connector member and to lock the polyaxial movement, fixing the first connector member relative to the first translation member; and a second locking member to secure the second elongate spinal fixation element in the engagement portion of the second connector member and to lock the polyaxial movement, fixing the first connector member relative to the first translation member.

In embodiments of the device including first and second connectors, the proximal portions of the first and second connector members may include a sphere and the proximal and distal portions of the translation member include a bore for receiving the sphere to provide the respective polyaxial movement. The engagement portions of the first and second connectors may further include proximal and distal arms, at least one of the proximal and distal arms resiliently flexing open to accept the respective first or second elongate spinal fixation element and flexing back to provisionally receive the respective first or second elongate spinal fixation element with the interference fit. Additionally, the first and second connector members may include a slit extending between the proximal portion of the first connector member to the distal portion of the first connector member, the slit allowing the resilient flexing of the at least one of the proximal and distal arms of the engagement portion of the first and second connectors. The first and second locking members may additionally include a set screw and a hole on the respective first or second connector member and operatively associated with the slit such that threading of the set screw into the hole moves the proximal and distal arms relative to one another to secure the respective first or second elongate spinal fixation element in the engagement portion of the respective first or second connector member.

Further provided for, in accordance with the disclosure, is a method for interconnecting first and second elongate spinal fixation elements, the method including: provisionally fitting the first elongate spinal fixation element into an engagement portion of a first connector with an interference fit, the first connector operatively associated with a translation member to provide polyaxial movement of the first connector member relative to the translation member; attaching the second elongate spinal fixation element to a second connector, the second connector coupled to the translation member; and locking a locking member provided on the first connector thereby securing the first elongate spinal fixation element in the engagement portion of the first connector member and locking the polyaxial movement in order to fix the first connector member relative to the first translation member. In some embodiments of the device, the locking member includes a first set screw and a hole on the first connector member, and the locking step of the method for interconnecting first and second elongate spinal fixation elements further includes threading the first set screw thereby simultaneously securing the first elongate spinal fixation element and locking the polyaxial movement. It is further contemplated within the disclosure that the interconnecting step of the method may be performed within a posterior spinal fusion construct.

In another embodiment, a device for coupling first and second vertebrae includes a first coupling element and a second coupling element. The first coupling element has a first body portion for receiving a first bone fastener and an elongate rod portion extending transversely from the first body portion. The second coupling element has a second body portion for receiving a second bone fastener and an extension portion extending transversely from the second body portion. The extension portion defines a recess sized and configured to receive the rod portion of the first coupling element. When unlocked, the rod portion is moveable in the recess to allow for rotational and translational movement of the first and second coupling elements. When locked, the relative position of the first and second coupling elements is fixed.

In yet another embodiment, a coupling assembly for securing first and second vertebrae includes first and second bone fasteners and first and second coupling elements. The first bone fastener has a head and a shaft extending therefrom. The shaft of the first bone fastener is configured to engage the first vertebra. The second bone fastener has a head and a shaft extending therefrom. The shaft of the second bone fastener is configured to engage the second vertebra. The first coupling element has a first body portion housing a first locking assembly and an elongate rod portion extending transversely from the first body portion. The first locking assembly includes a rotatable locking member, a clamp portion, and a ring portion configured to at least partially surround a portion of the locking member and the clamp portion. The head of the first bone fastener is received in the clamp portion of the first locking assembly. The second coupling element has a second body portion housing a second locking assembly and an extension portion extending transversely from the second body portion. The extension portion defines a recess for receiving the rod portion of the first coupling element. The second locking assembly includes a rotatable locking member, a clamp portion, and a ring portion configured to at least partially surround a portion of the locking member and the clamp portion. The head of the second bone fastener is received in the clamp portion of the second locking assembly. When unlocked, the rod portion is moveable in the recess to allow for rotational and translational movement of the first and second coupling elements, and when locked, the relative position of the first and second coupling elements is fixed.

In another embodiment, a method for affixing a coupling device to adjacent vertebrae includes securing a first bone fastener to a pedicle of a first vertebra; securing a second bone fastener to a pedicle of a second vertebra; attaching a coupling device to the first and second bone fasteners; moving the rod portion relative to the extension portion to allow for rotational and translational movement of the first and second coupling elements; and locking the position of the rod portion in the recess to fix the first coupling element relative to the second coupling element.

In yet another embodiment, a coupling device includes a coupling element having a body portion for receiving a bone fastener and an extension portion extending transversely from the body portion; and a locking assembly received in the coupling element, the locking assembly including a locking member, a clamp portion, and a ring portion, wherein the locking member is configured to contact an upper portion of the clamp portion and the ring portion is configured to at least partially surround a lower portion of the clamp portion. When unlocked, the bone fastener is moveable within the clamp portion to allow for polyaxial movement of bone fastener relative to the coupling element, and when locked, the bone fastener is fixed relative to the coupling element.

In a further embodiment, a coupling assembly includes a first bone fastener having a head and a shaft extending therefrom, the shaft configured to engage the first vertebra; a first coupling element having a first body portion housing a first locking assembly and an extension portion extending transversely from the first body portion, the first locking assembly comprising a rotatable locking member, a clamp portion, and a ring portion configured to at least partially surround a portion of the clamp portion, and the head of the first bone fastener is received in the clamp portion. When unlocked, the first bone fastener is moveable in the clamp portion to allow for polyaxial movement of the bone fastener relative to the first coupling element, and when locked, the position of the bone fastener is fixed relative to the first coupling element.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 3 is a perspective view of the connector member of the device of FIG. 1;

FIG. 4 is a cross-sectional view of the connector member of FIG. 3;

FIG. 5 is a cross-sectional view of the translation member of the device of FIG. 1 illustrating a dove-tail connection;

FIG. 6 is a perspective view of the translation member of the device of FIG. 1;

FIG. 8A is a side view of a closed offset connector member in accordance with the disclosure;

FIG. 8B is a cross-sectional view of the closed offset connector member of FIG. 8A;

FIG. 8C is an exploded view of the locking assembly of the closed offset connector member of FIG. 8A;

FIG. 8D is an assembled view of the locking assembly of the closed offset connector member of FIG. 8A;

FIG. 10A is a side perspective view of a closed head tulip element in accordance with the disclosure;

FIG. 10B is a cross-sectional view of the closed-head tulip element of FIG. 10A;

FIG. 11A is a side perspective view of a headed rod member in accordance with the disclosure;

FIG. 11B is a cross-sectional view of the headed rod member of FIG. 11A;

FIG. 11C is an exploded view of the locking assembly of the headed rod member of FIG. 11A;

FIG. 11D is an assembled view of the locking assembly of the headed rod member of FIG. 11A;

FIG. 12A is a side perspective view of a one-level connector in accordance with the disclosure;

FIG. 12B is a cross-sectional view of the one level connector of FIG. 11A;

FIG. 12C is an exploded view of the locking assembly of the one level connector of FIG. 12A;

FIG. 12D is an assembled view of the locking assembly of the one level connector of FIG. 12A;

DETAILED DESCRIPTION OF THE INVENTION

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language).

Figure 1:
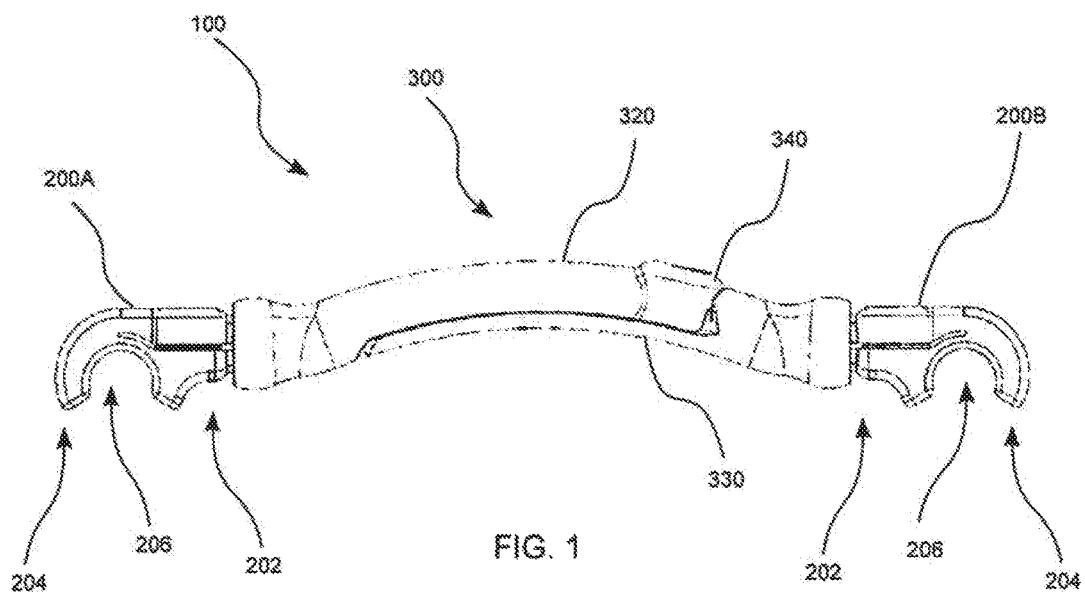
FIG. 1 is a side view of an embodiment of the cross connector device in accordance with the disclosure.

Referring now to FIG. 1, a device 100 of the disclosure is illustrated prior to receiving first and second spinal fixation elements (not illustrated). Device 100 includes first and second connector members 200A, 200B designed to receive a fixation element, and a translation member 300 cross-connecting or transconnecting first connector member 200A with second connector member 200B. In the embodiment illustrated, first connector member 200A is substantially similar to second connector member 200B, and connector members 200A, 200B are associated with opposing ends of translation member 300. Although it is advantageous to have dual connector members 200A, 200B, it should be understood that the disclosure contemplates a single connector member 200A for receiving the first fixation element while another connector, such as the alternative connectors disclosed herein or other connectors known or to be developed, connected to translation member 300 for receiving the second fixation element. Accordingly, the disclosure contemplates device 100 including any combination of connector members 200.

The spinal fixation elements to be received may include rods, plates, or other elongate members to be utilized in a spinal fixation construct, such as a posterior fusion procedure, although a variety of known or to be developed spinal fixation elements are contemplated within the disclosure. A variety of elongate member sizes are contemplated, according to the construct or situation of the surgical procedure to be performed. Examples of rod or member sizes contemplated include, but are not limited to, diameters of 4.75 mm, 5.5 mm, 6.35 mm, and other rods or members of similar sizes known or to be discovered for use in spinal fixation procedures.

Additionally referring to FIGS. 3 and 4, connector members 200A, 200B have a proximal portion 202, generally referring to the portion of connector member 200A, 200B in proximity to the translation member 300, and a distal portion 204, generally referring to the portion of the connector member 200A, 200B opposite from translation member 300. An engagement portion 206 is provided on distal portion 204 for receiving a fixation element. Proximal portion 202 is operatively associated with translation member 300 to permit polyaxial movement, including rotational movement, of connector member 200A, 200B with respect to translation member 300. Additionally provided on connector member 200A, 200B is a locking member 210, illustrated in FIGS. 3 and 4 as a set screw, operative to secure a received fixation element in engagement portion 206 while also fixing movement of connector member 200A, 200B with respect to translation member 300, i.e. locking the polyaxial movement.

Locking member 210, as illustrated in the embodiment of FIGS. 3 and 4, includes a locking screw 212 received in a threaded hole or bore 214 provided on connector member 200A, 200B. As a result of a threading or rotating, from an applied torsional force on a tool receiving upper surface of screw 212, of locking screw 212 within hole 214, screw 212 advances into hole 214 and into or towards a gap or slit 220 which extends between distal and proximal portion 202, 204. Accordingly, by displacing screw 212 into gap 220, the gap is splayed at both the distal and proximal portions 202, 204, resulting in simultaneously securing a fixation element received within engagement portion 206 as well as fixing or locking the polyaxial and rotational movement of the connector member 200A, 200B with respect to translation member 300. The splaying may be assisted by a gap wedge 222 positioned between hole 214 and gap 220 so as to exert a splaying force on gap 220 as screw 212 advances into hole 214 and presses against wedge 222.

An elongate fixation member is provisionally securable in engagement portion 206 through a snap-fit or an interference connection. Engagement portion 206 includes proximal and distal arms 208A, 208B for receiving an elongate fixation member. As an elongate fixation member is introduced into engagement portion 206, at least one of arms 208A, 208B resiliently flex open to accept the elongate fixation element and flex back to provisionally receive the fixation element with an interference fit. The interference fit may be tightened, securing the received spinal fixation element, by splaying the distal portion of gap 220. The splaying or separating of the distal portion of gap 220 widens the gap thereby moving arms 208A, 208B with respect to one another resulting in a clamping motion on a received fixation member.

Extending into a bore 310 of translation member 300 is a sphere 230 for providing polyaxial movement of connection member 200A, 200B with respect to translation member 300. The polyaxial movement is advantageous in aiding a surgeon, or other technician, installing the device to move, rotate, or adjust device 100 to connect second connector member 200B with the second elongate member while the first elongate member is provisionally received within engagement portion 206 of first connector member 200A. Once the second elongate member is connected to or secured within second connector member 200B, the polyaxial movement of first connector 200A may be fixed by locking sphere 230 within bore 310. In an embodiment of the disclosure, sphere 230 is composed of upper and lower surfaces 232, 234, separated by the proximal portion of gap 220. Locking of sphere 230 within bore 310 may accordingly occur by splaying upper and lower surfaces 232, 234 thereby forcing surfaces 232, 234 against an inner wall or surface 312 of bore 310 in order to frictionally secure sphere 230 from moving or rotating within bore 310. In some embodiments, sphere 230 will advantageously include grooves or ridges 236 provided on surfaces 232, 234 and mateable with corresponding grooves or ridges 314 provided on inner surface 312.

Splaying of both the distal and proximal portions of gap 220 advantageously result from turning or rotating locking screw 212. As screw 212 is rotated, distal and proximal portions of gap 220 are both splayed thereby securing the received elongate fixation member in engagement portion 206 as well as thereby fixing connector member 200A, 200B from polyaxial movement with respect to translation member 300. This dual locking mechanism is advantageous for quickly and efficiently securing device 100 during a surgical procedure.

Figure 2:
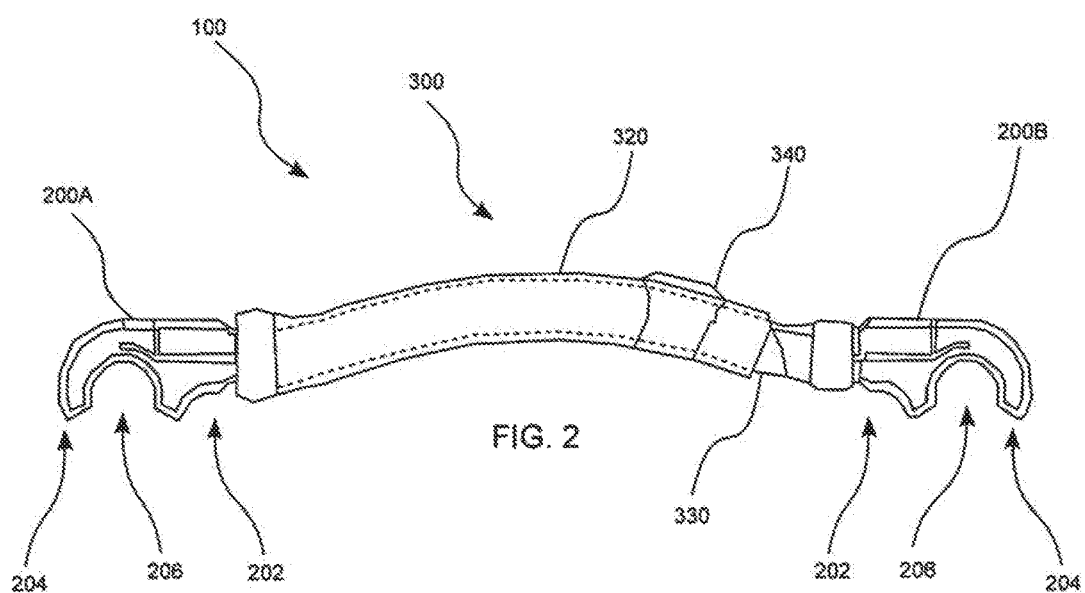
FIG. 2 is a side view of a second embodiment of a cross connector device.
Figure 7A:
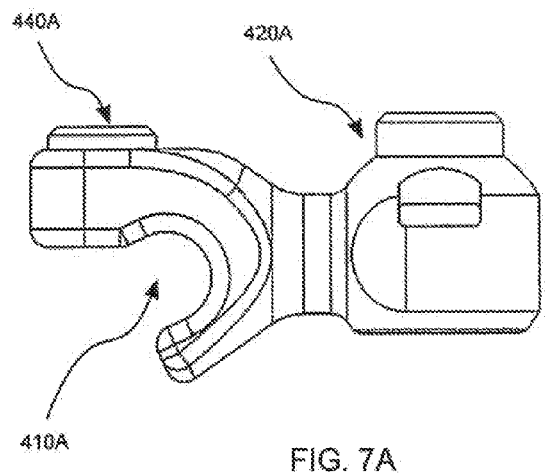
FIG. 7A is a side view of the an open offset connector member in accordance with the disclosure.
Figure 7B:
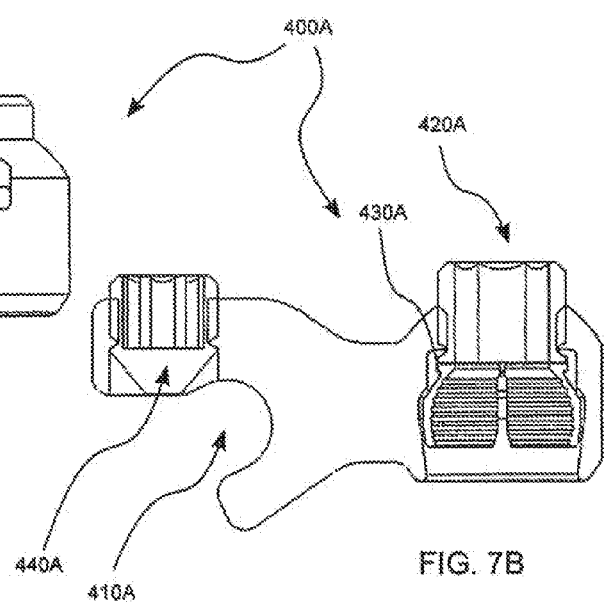
FIG. 7B is a cross-sectional view of the open offset connector member of FIG. 7A.
Figure 7C:
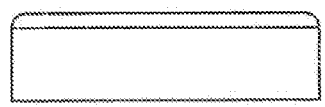
FIG. 7C is an exploded view of the locking assembly of the open offset connector member of FIG. 7A.
Figure 7D:
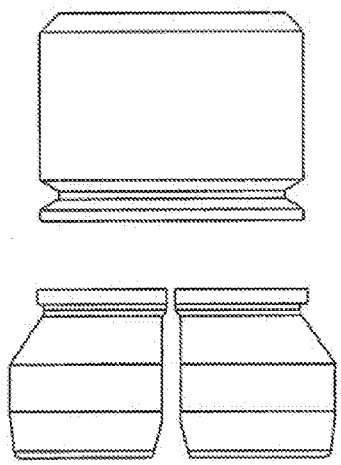
FIG. 7D is an assembled view of the locking assembly of the open offset connector member of FIG. 7A.
Figures 9A, 9B:
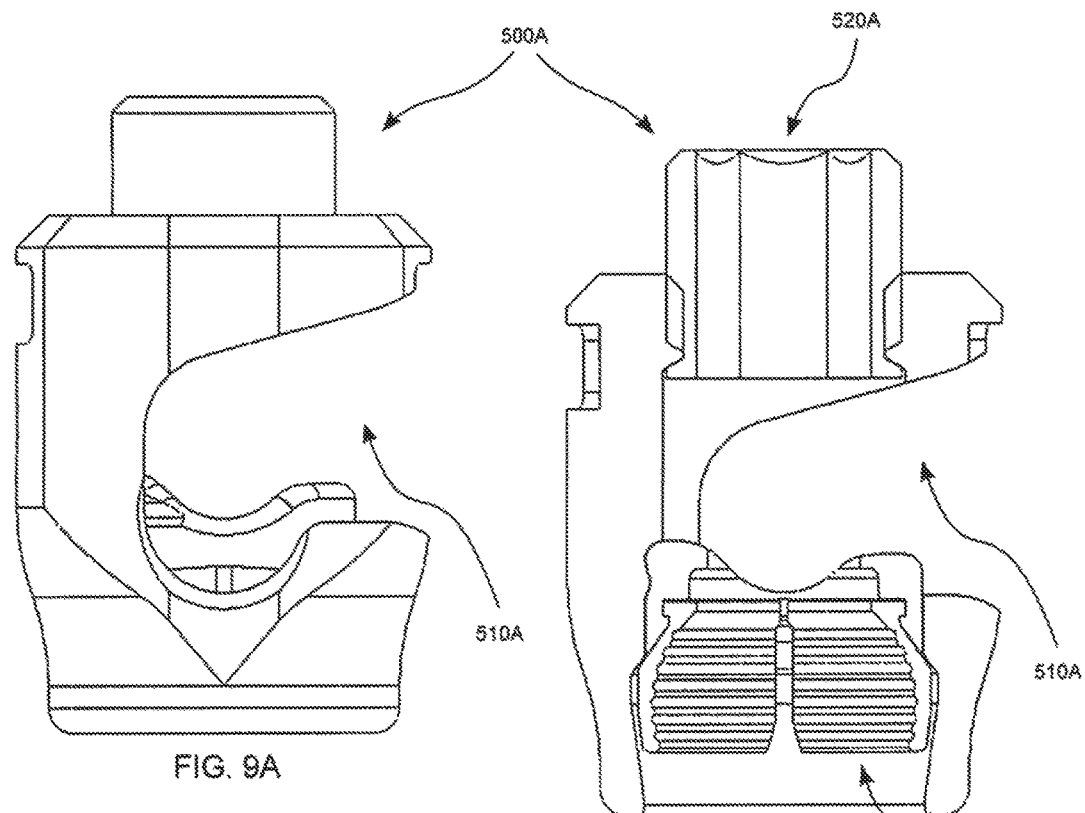
FIG. 9A is a side perspective view of a side-loading tulip element in accordance with the disclosure.
FIG. 9B is a cross-sectional view of the side-loading tulip element of FIG. 9A.
Figures 9C, 9D:
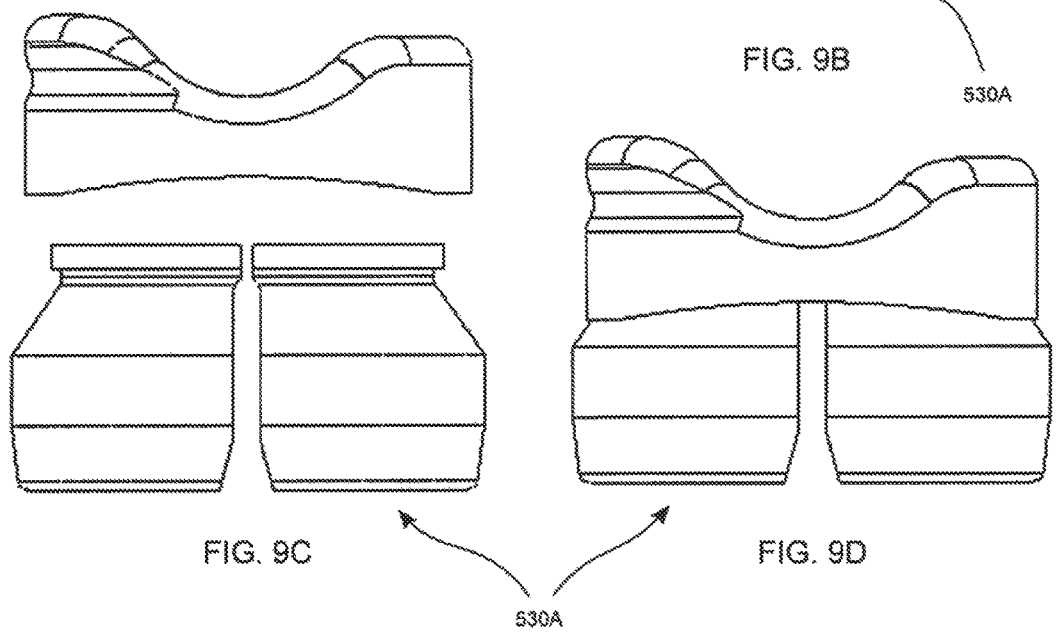
FIG. 9C is an exploded view of the locking assembly of the side-loading tulip element of FIG. 9A.
FIG. 9D is an assembled view of the locking assembly of the side-loading tulip element of FIG. 9A.

In reference now to FIGS. 5 and 6, an embodiment of translation member 300 includes first and second translation elements 320, 330. First translation element 320 is connectable with first connector member 200A and second translation element 330 is connectable with second connector member 200B. First and second translation elements 320, 330 are movable or slidable relative to one another to adjust a distance between first and second connector members 200A, 200B. This translation movement adjusting the distance between first and second connector members 200A, 200B along with polyaxial movement of connector members 200A, 200B with respect to translation member 300, provides for interconnecting first and second fixation elements. In one embodiment, first and second translation elements 320, 330 move relative to one another along an arced path. In FIG. 2, an additional embodiment is illustrated depicting second translation element 330 slidable within first translation element 320, and fixable by a third locking screw or element 340.

A locking element 340 is provided to couple first and second translation elements 320, 330 with respect to each other, thereby fixing first and second translation elements 320, 330 from moving with respect to each other and securing first and second connector elements 200A, 200B at a distance from each other. In an exemplary embodiment, locking element 340 couples first and second translation elements 320, 330 in a dovetail connection. A dovetail connection, as shown in the illustrated embodiments of FIGS. 5 and 6, provides a strong yet flexible geometry, arcing over a spinal column situated between first and second connection members 200A, 200B. With a dovetail connection, translation, with little or no rotation between translation elements 320, 330 is provided. In the embodiment illustrated in FIG. 2, first element 320 may operate to internally receive second element 330, both elements 320, 330 slidable and rotatable with respect to each other thereby establishing a distance between first and second connector members 200A, 200B.

It is contemplated within the disclosure that device 100 can be utilized as a cross-connector option for a spinal stabilization system, for example interconnecting first and second spinal fixation rods within a posterior spinal fusion construct. Device 100, in addition to the previously disclosed connector options as well as the additional connector options described herein, are components of a modular system which allows for screw tulip assembly to be attached to the screw head in-situ, following operations including, but not limited to: intervertebral operations, decortication, fusion bed preparation, etc. In reference now to FIGS. 7-13, additional embodiments of connector options which may be utilized in a spinal stabilization system will now be described.

FIGS. 7A-7D illustrate an open offset connector 400A, in accordance with the disclosure, which includes an engagement portion 410A for receiving a fixation element, a second locking set screw 420A with locking assembly 430A, and a second locking set screw 440A for securing the received fixation element. Similar to connector members 200A, 200B, the engagement portion may be advantageously received in a preliminary snap-fit or interference connection at engagement portion 410A. Second locking set screw 440A is provided to lock or clamp a received fixation element within engagement portion 410A as screw 440A is rotated or advanced into connector 400A. Open offset connector 400A may be offered in both modular and preassembled configurations allowing for an extremely low profile iliac fixation point, which is particularly advantageous for surgical procedures performed on small stature patients.

FIGS. 8A-8D illustrate a closed offset connector 400B, in accordance with the disclosure, which includes engagement portion 410B, a first locking set screw 420A with locking assembly 430, and a second locking set screw 440B for securing the received fixation element. Unlike engagement portion 410A, engagement portion 410B is closed to fully enclose a received spinal fixation element. In the embodiment disclosed, second locking set screw 420B is similar to second locking set screw 420A, and locking assembly 430B is similar to locking assembly 430A, however it should be appreciated that different locking assemblies and/or set screws for establishing bone fixation, such as iliac fixation points, may be utilized in accordance with the disclosure. Closed offset connector 400B may also be offered in both modular and preassembled configurations allowing for extremely low profile fixation points.

Referring now to FIGS. 9A-9D and FIGS. 10A-10D illustrating embodiments of tulip elements 500A, 500B which may be utilized as part of a stabilization system, in accordance with the disclosure. Side-loading tulip element 500A, includes a tulip 510A, locking set screw 520A, and a locking assembly 530A. Closed head tulip element 500B includes a tulip 510B, locking set screw 520B, and a locking assembly 530B associated with locking screw 520B. Tulip elements 500A, 500B may be offered in both modular and preassembled configuration and allow for a secure low profile fixation rod and bone screw or fastener connection point, which is particularly useful for iliac fixation in a spinal fixation procedure.

FIGS. 11A-11D illustrate a headed rod or implant 600 which may be utilized as part of a stabilization system, in accordance with the disclosure. Implant 600 includes a connector element or rod 610, locking set screw 620, and a locking assembly 630 associated with locking set screw 620. Headed rod 600 may be offered in both modular and preassembled configurations and allows for extremely low profile fixation points, for example in sacral fixation points, which is useful for small stature patients.

FIGS. 12A-12D illustrate a one level connector 700 which may be utilized as part of a stabilization system, in accordance with the disclosure. One-level connector includes first and second locking set screws 710A, 710B and first and second locking assemblies 720A, 720B associated with locking set screws 710A, 710B. One level connector 700 may be offered in both modular and preassembled configurations and allows for extremely low profile fixation points, for example in sacral fixation points, which is useful for small stature patients.

Figure 13A:
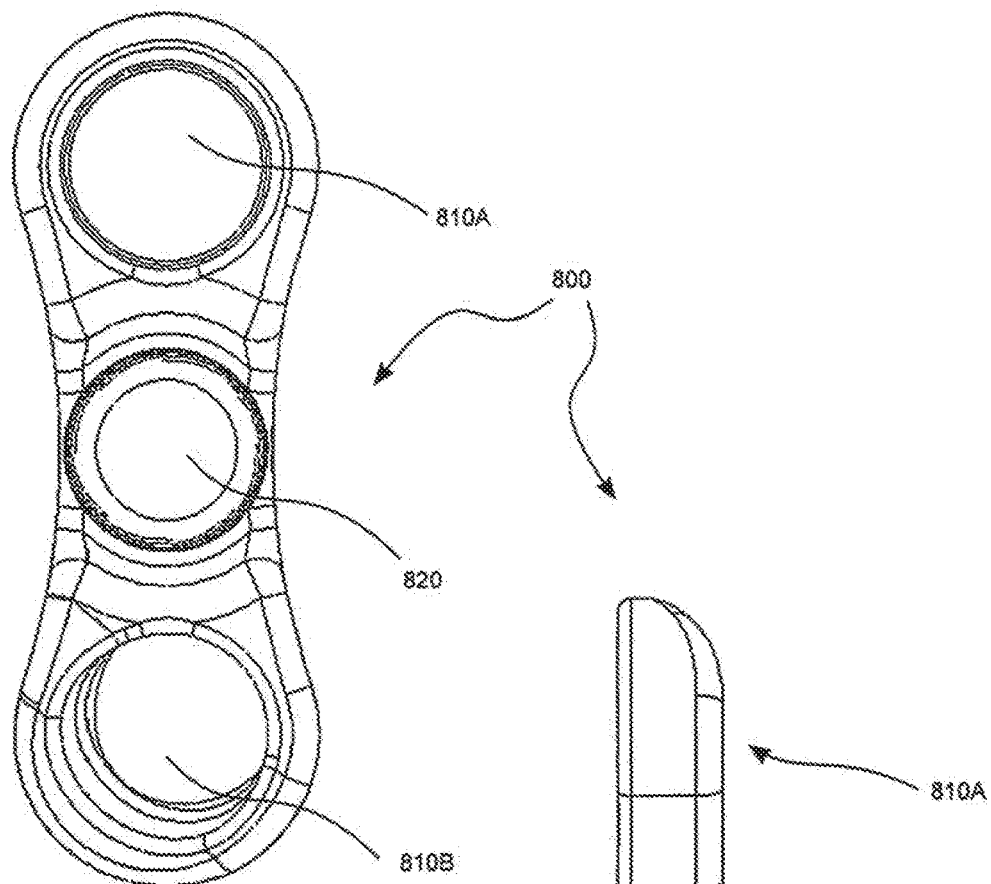
FIG. 13A is a top view of a fixation plate in accordance with the disclosure.
Figure 13B:
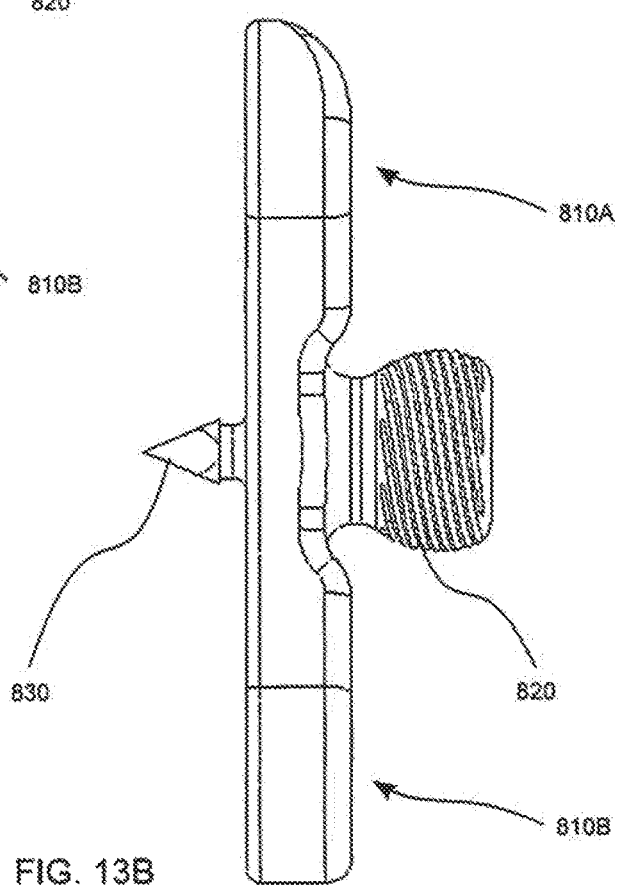
FIG. 13B is a side view of the fixation plate of FIG. 13A.

FIGS. 13A and 13B illustrate a fixation plate or implant 800 which may be utilized as part of a stabilization system, including for example sacral fixation, in accordance with the disclosure. Fixation plate 800 advantageously accommodates dual-point fixation by receiving a first rod or fixation element in a first aperture 810A, and a second rod or fixation element in a second aperture 810B, thereby allowing in-situ attachment of any modular component as a part of a stabilization system. Provided on a first end of plate 800 is a protruding element 820, which in some embodiments is threaded on an exterior surface in order to mate with another element and/or to improve the grip of a technician attaching the plate as a component of a stabilization system. Provided on a surface of the plate opposite protruding element or knob 820 is a pointed element or spike 830. The one-piece design, as shown in the illustrated embodiment of plate 800, is beneficial for both manufacturing and ease of attachment as a component of a stabilization system. The dual-point fixation provided by plate 800 has shown to at least 25% stronger than traditional constructs used in similar sacral fixation elements.

Figure 14A:
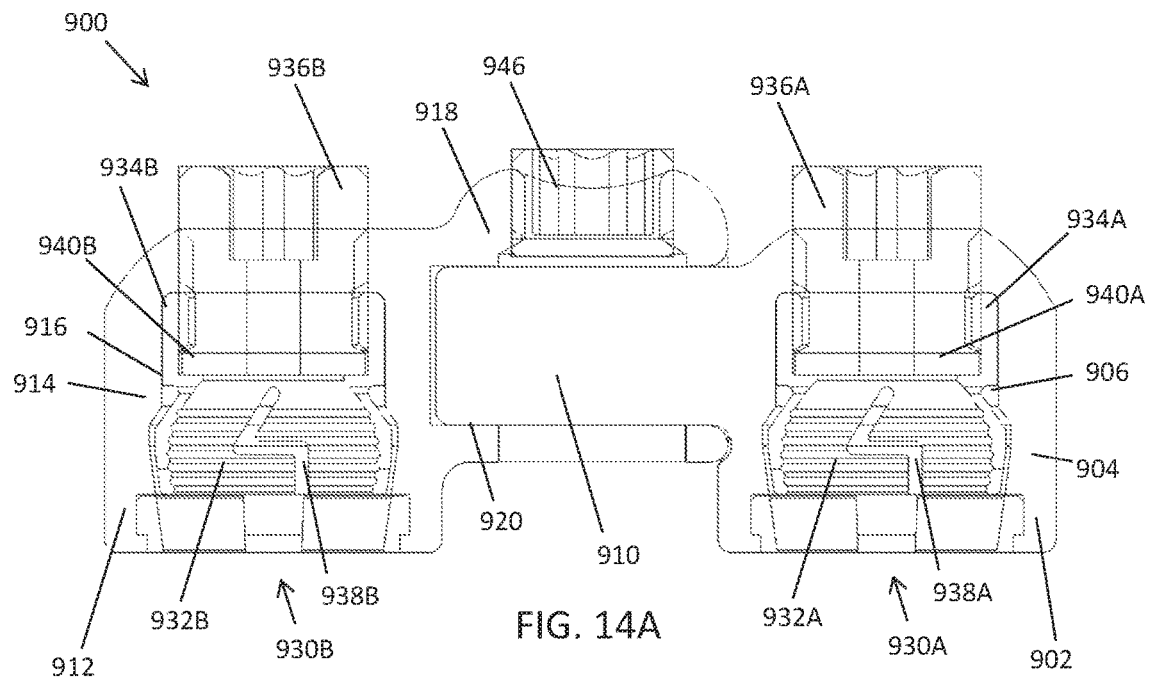
FIG. 14A is a cross-sectional view of an embodiment of a one-level connector device.
Figure 14B:
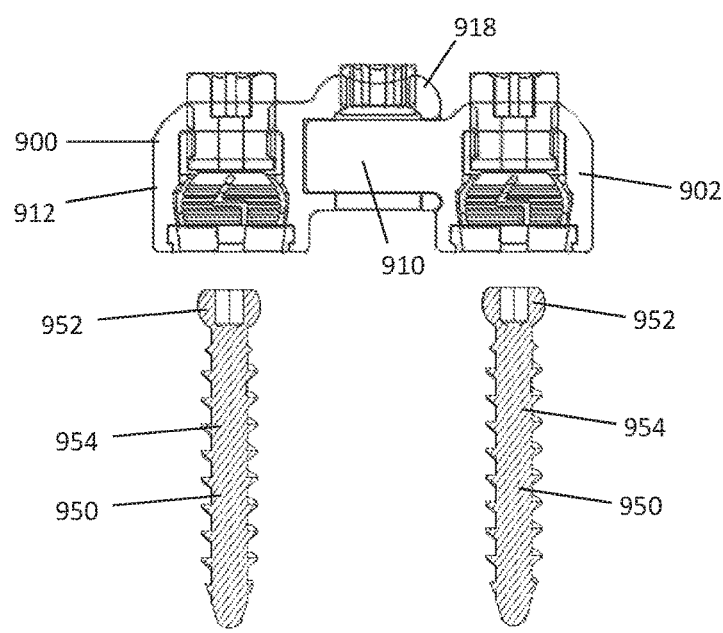
FIG. 14B is an exploded cross-sectional view of a pedicle-based assembly including the connector device of FIG. 14A.

FIGS. 14A and 14B illustrate another embodiment of a connector 900 that may be utilized as part of a stabilization system. In particular, the connector 900 may be a low profile, one-level connector that attaches directly to pedicle screws 950. The one-level connector 900 allows for controlled rotational movement and compression and/or elongation until final tightening of the construct. The low profile design may be especially useful for very small stature patients.

As shown in FIG. 14A, the one-level connector 900 includes a first coupling element 902 and a second coupling element 912. The first and second coupling elements 902, 912 are configured such that the first coupling element 902 can be rotated relative to the second coupling element 912 or vice versa. The first and second coupling elements 902, 912 are also configured such that the first and second coupling elements 902, 912 are able to move toward one another and away from one another, thereby providing compression or distraction of adjacent vertebrae when the connector 900 is attached to the vertebrae.

As best seen in the exploded view in FIG. 14B, the assembly includes a one-level connector 900 and two bone fasteners 950 configured to be engaged by the connector 900. The bone fasteners 950 may each include a head 952 and a threaded shaft 954 that extends from the head 952. In this embodiment, the head 952 is generally rounded and shaped to form a portion of a ball or at least a portion of a sphere. Thus, when received in the connector 900, the head 952 may allow for polyaxial movement of the fastener 950. It is contemplated that the bone fastener 950 may be configured to move polyaxially, monoaxially, or uni-planar with respect to the connector 900. The head 952 may be substantially smooth, partially or fully threaded, or otherwise textured. The threaded shaft 954 may have a blunt tip, a sharp point, or the like and may be tapered along its length. The threaded shaft 954 is configured to engage bone, and may be particular suitable for being secured in the pedicle of a vertebra. Threaded cutting flutes may be provided for self-tapping. The screw head 952 may include any suitable driving recess, e.g., a hexalobular recess, for screw insertion.

With further emphasis on FIG. 14A, the connector 900 includes a first coupling element 902 configured to receive the head 952 of the first bone fastener 950. The first coupling element 902 includes a body portion 904 and an opening 906 extending longitudinally through the body portion 904. The locking assembly 930A including locking set screw 936A may be sized and dimensioned to be received in the opening 906 in the body portion 904 of the first coupling element 902. The head 952 of the fastener 950 may be sized and dimensioned to be received within a portion of the locking assembly 930A as described in more detail herein. The first coupling element 902 may further include a connector element or rod portion 910 extending transversely from the body portion 904. The rod portion 910 may include an elongate cylindrical portion or may have a cross-section that is substantially square, round, elliptical, or of any other suitable shape. In a preferred embodiment, the rod portion 910 is substantially cylindrical in shape to allow for controlled rotation of the first coupling element 902 relative to the second coupling element 912. The first coupling element 902 may be similar to implant 600 described elsewhere herein.

The locking assembly 930A may be similar to the other locking assemblies described herein. The locking assembly 930A includes a clamp portion 932A, a ring portion 934A, and a locking set screw 936A. The locking set screw 936A includes a base portion 940A and an engagement portion having any suitable driving recess, e.g., a hexalobular recess, for locking and unlocking of the set screw 936A. The locking set screw 936A may include threaded or non-threaded locking features designed to allow for a locked position and an unlocked position, for example, when the set screw 936A is rotated. The base portion 940A is configured to be received in the ring portion 934A and optionally into contact with a top face of the clamp portion 932A when the locking set screw 936A is locked. The ring portion 934A may be configured to surround the locking set screw 936A and an upper portion of the clamp portion 932A. When the locking set screw 936A is locked, the head 952 of the bone fastener 950 is locked in the first coupling element 902 and is locked into position relative to the first coupling element 902.

The clamp portion 932A of the locking assembly 930A is configured to at least partially surround the head 952 of the fastener 950. The head 952 may be received in the clamp portion 932A, for example, with a provisional interference fit. When unlocked, the clamp portion 932 may be configured to move or articulate to allow, for example, polyaxial movement of the bone fastener 950. The clamp portion 932A may have an outer surface, for example, with a plurality or protrusions and recesses, a threaded portion, or other texture. The clamp portion 932A may also include at least one slit 938A extending therethrough to allow the clamp portion 932A to be compressed around the head 952 of the fastener 950 when the locking assembly 930A is locked. The slit 938A may extend from a top portion to a bottom portion of the clamp portion 932A and may extend completely or partially therethrough. The slit 938A may be linear or non-linear in shape. As shown in FIG. 14A, the slit 938 may have an angled portion, a perpendicular portion extending substantially transverse to the longitudinal axis, and a longitudinal portion extending along the longitudinal axis of the body portion 904 of the first coupling element 902. The configuration and number of slits 938A may be selected to obtain the desired amount of compression on the head 952 of the fastener 950.

When the locking assembly 930A is in its locked position, the locking set screw 936A can be advanced through the body portion 904 to engage the ring portion 934A and/or the clamp portion 932A, thereby applying downward force onto clamp portion 932A and securing the bone fastener 950 to the first coupling element 902. In one embodiment, the locking set screw 936A forces the ring portion 934A downward and into contact with the clamp portion 932A causing the locking assembly 930A to move downward in the first coupling element 902 and secure the fastener 950 in its final implanted position.

The one-level connector 900 includes a second coupling element 912 configured to receive the head 952 of the second bone fastener 950. The second coupling element 912 may include a body portion 914 having an opening 916 extending longitudinally therethrough. The locking assembly 930B may be sized and dimensioned to be received in the opening 916 in the body portion 914 of the second coupling element 912. The locking assembly 930B includes clamp portion 932B having slit 938B, ring portion 934B, and locking set screw 936B including base portion 940B. The components and functionality of locking assembly 930B are substantially the same as for locking assembly 930A and are therefore not repeated in detail for brevity, but would apply equally for locking assembly 930B.

The second coupling element 912 includes an extension portion 918 defining a recess 920 therein. The extension portion 918 may extend substantially transverse from the coupling element 912. The recess 920 may be in the form of a blind hole. The recess 920 may extend through the length of the extension portion 918. The recess 920 may terminate before the body portion 914 or optionally may enter the body portion 914. The recess 920 may be dimensioned and configured to receive the rod portion 910 of the first coupling element 902. Accordingly, the recess 920, extending a distance into the extension portion 918, may have an elongate cylindrical portion or may have a cross-section that is substantially square, round, elliptical, or any other shape that substantially corresponds to the outer dimensions of the rod portion 910 of the first coupling element 902. Although depicted with the first coupling element 902 having the rod portion 910 and the second coupling element 912 having the extension portion 918 with the recess 920, which receives the rod portion 910, it will be appreciated that these components may be reversed such that the first coupling element 902 is provided with a recess and the second coupling element 912 is provided with a rod portion to be received within the recess or any other suitable configuration.

The rod portion 910 is configured to be received within the recess 920 in the extension portion 918 such that controlled rotational movement and compression and/or elongation may be obtained by the user. In particular, the body portion 904 of the first coupling element 902 may be rotated relative to the body portion 914 of the second coupling element 912. By rotating the first and second coupling elements 902, 912 with respect to one another, the first and second bone fasteners 950 may be offset to one another at a desired angle. If rotation is not desired, the first and second bone fasteners 950 may be aligned with one another.

The body portion 904 of the first coupling element 902 may also be moved in a general direction towards or away from the body portion 914 of the second coupling element 912, thereby shortening or lengthening the relative length of the overall connector 900 in order to apply a compressive or distractive force to the vertebrae. When the overall length of the connector 900 is shortened to its smallest length, the end of the rod portion 910 may abut the innermost portion of the recess 920 and/or an outermost portion of the extension 918 may abut the outside of the body portion 904. When the overall length of the connector 900 is increased, a gap forms between the end of the rod portion 910 and the innermost portion of the recess 920 and/or the outermost portion of the extension 918 and the outside of the body portion 904. The gap will increase as the length of the connector 900 is increased until a maximum length is obtained.

Once the desired orientation including rotation and distance between the first and second coupling elements 902, 912 is achieved, the relative position can be locked by locking member or locking set screw 946 positioned in extension portion 918 of the second coupling element 912. The locking set screw 946 may also include any suitable driving recess, e.g., a hexalobular recess, for locking and unlocking of the set screw 946. The locking set screw 946, similar to locking set screws 936A, 936B, may include threaded or non-threaded locking features designed to allow for a locked position and an unlocked position, for example, when the set screw 946 is rotated. The locking set screw 946 may be configured to apply a force on the rod portion 910 of the first coupling element 902, for example, when the locking set screw 946 is moved downward and into contact with an outer surface of the rod portion 910 of the first coupling element 902. The rod portion 910 may also be configured with an indentation or groove (not shown), for example, to receive the bottom surface of the locking set screw 946 when locked.

According to a method, the connector 900 may be used to perform a one-level spinal fusion. For example, the posterior aspects of the spine may be exposed or accessed via a minimally invasive surgical (MIS) approach. A first bone fastener 950 may be inserted into the pedicle of a first vertebra and a second bone fastener 950 may be inserted into the pedicle of a second, adjacent vertebra. The bone fasteners 950 are preferably inserted such that the heads 952 remain proud above the bone. After the bone fasteners 950 are secured, the connector 900 may be attached to the heads 952 of the respective bone fasteners 950. In particular, the heads 952 of the bone fasteners 950 may be received in the respective first and second coupling elements 902, 912. The first and second coupling elements 902, 912 may provisionally receive the fasteners 950, for example, with an interference fit.

The relative position of the connector 900 and fasteners 950 may be modified or changed until the desired orientation is achieved. In particular, the length of the connector 900 may be expanded or contracted by translating the rod portion 910 in the recess 920 of the extension portion 918. In addition, the first coupling element 902 may be rotated relative to the second coupling element 912 such that the bone fasteners 950 are angled with respect to one another. The rotational and translational movement of the connector 900 may occur simultaneously or sequentially in any suitable order. It is also contemplated that the fasteners 950 are polyaxially rotated and positioned with respect to the connector 900.

Once the final positioning has been obtained, the locking set screws 936A, 936B, and 946 may be tightened to achieve the final construct. The locking set screws 936A, 936B, and 946 may be tightened sequentially, in any suitable order, or simultaneously. Although not depicted, the locking set screw 936A, 936B, and 946 may also include a back-out prevention feature. The locking set screws 936A, 936B secure the fasteners 950 in the respective first and second coupling elements 902, 912, and the locking set screw 946 secures the rod portion 910 of the first coupling element 902 within recess 920 in the extension portion 918 of the second coupling element 912, thereby locking the length and rotational position of the connector 900. Thus, the low profile connector 900 allows for controlled rotational relationships and compression or elongation after final tightening of the construct.

Turning now to FIGS. 15-18, alternative components for a modular system which allow for attachment to one or more bone fasteners, such as pedicle screws 950 and/or one or more elongate fixation elements, such as elongate rods 960 are shown. The modular components may include headed rods, open offset connectors, closed offset connectors, one-level connectors, and the like. The features from one embodiment may be used in any other embodiment. The modular components may be suitable, for example, for intervertebral operations, decortication, fusion bed preparation, etc. The components may be connected to new or existing constructs.

Figure 15A:
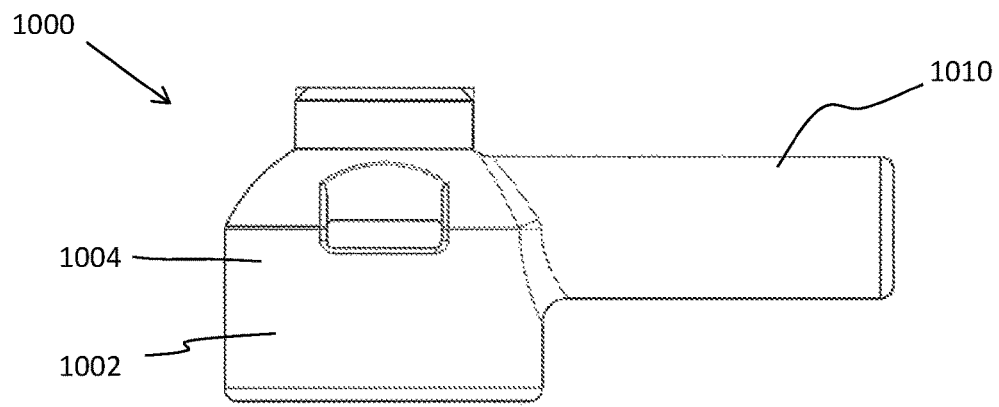
FIG. 15A is a side perspective view of a headed rod member in accordance with another embodiment.
Figure 15B:
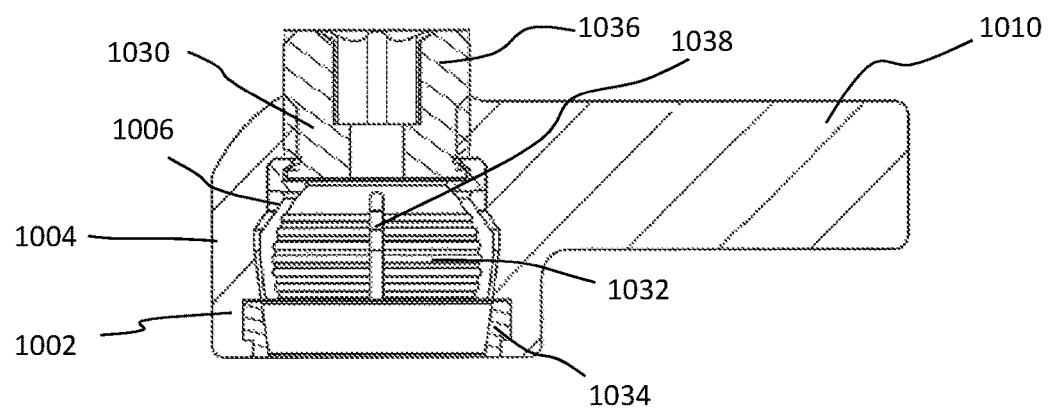
FIG. 15B is a cross-sectional view of the headed rod member of FIG. 15A.
Figure 15C:
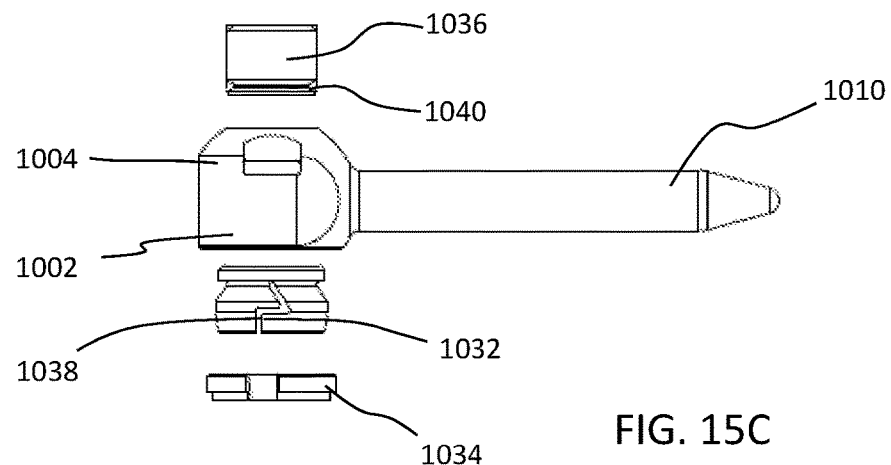
FIG. 15C is an exploded view of a headed rod member according to another embodiment.

FIGS. 15A-15C illustrate a headed rod or implant 1000 which may be utilized as part of a stabilization system. Implant 1000 includes a connector or coupling element 1002 with an integral rod 1010. Headed rod 1000 may be offered in both modular and preassembled configurations and allows for extremely low profile fixation points, for example in sacral fixation points, which is useful for small stature patients.

The headed rod connector or implant 1000 may be a low profile connector that attaches directly to a bone fastener, such as a pedicle screw 950. As shown in FIG. 15B, the implant 1000 includes a coupling element 1002 configured to receive the head 952 of the pedicle screw 950. When received in the connector 1000, the head 952 may allow for polyaxial movement of the fastener 950 relative to the coupling element 1002. It is also contemplated that the bone fastener 950 may be configured to move polyaxially, monoaxially, or uni-planar with respect to the connector 1000.

The coupling element 1002 includes a body portion 1004 and an opening 1006 extending longitudinally through the body portion 1004. A locking assembly 1030 or a portion thereof may be sized and dimensioned to be received in the opening 1006 in the body portion 1004 of the coupling element 1002. The head 952 of the fastener 950 may be sized and dimensioned to be received within a portion of the locking assembly 1030 as described in more detail herein.

The coupling element 1002 may further include a connector element or rod portion 1010 extending transversely from the body portion 1004. The rod portion 1010 may be substantially integral with the coupling element 1002, for example, extending from an upper portion or central portion of the coupling element 1002. The rod portion 1010 may have a length greater than the width or outer diameter of the coupling element 1002. The rod portion 1010 may terminate at a free end. For example, the rod portion 1010 may terminate a given distance away from the coupling element

1002. The free end of the rod portion 1010 may be blunt, pointed, or otherwise configured. The rod portion 1010 may include an elongate cylindrical portion or may have a cross-section that is substantially square, round, elliptical, or of any other suitable shape. The rod portion 1010 may be sized and dimensioned to be received in a traditional tulip element (not shown). In a preferred embodiment, the rod portion 1010 is substantially cylindrical in shape to couple to a traditional tulip assembly, for example, comprising a second pedicle screw.

The locking assembly 1030 may include similar features to the other locking assemblies described herein. As best seen in the exploded view in FIG. 15C, the locking assembly 1030 includes a clamp portion 1032, a ring portion 1034, and a locking set screw 1036. The locking set screw 1036 includes a base portion 1040 and an engagement portion having any suitable driving recess, e.g., a hexalobular recess, for locking and unlocking of the set screw 1036. The locking set screw 1036 may include threaded or non-threaded locking features designed to allow for a locked position and an unlocked position, for example, when the set screw 1036 is rotated. The base portion 1040 is configured to contact a top face of the clamp portion 1032 when the locking set screw 1036 is locked. The ring portion 1034, for example, in the form a snap ring, may be configured to surround the base of the clamp portion 1032. The ring portion 1034 may be configured to substantially seat in the bottom of the coupling element 1002. The ring portion 1034 may form a complete or partial ring, for example, with a gap separating first and second ends of the ring portion 1034. When the locking set screw 1036 is locked, the ring portion 1034 surrounds the lower portion of the clamp portion 1032 and is seated in the base of the coupling element 1002, thereby locking the head 952 of the bone fastener 950 in the coupling element 1002.

The clamp portion 1032 of the locking assembly 1030 is configured to at least partially surround the head 952 of the fastener 950. The head 952 may be received in the clamp portion 1032, for example, with a provisional interference fit. When unlocked, the clamp portion 1032 may be configured to move or articulate to allow, for example, polyaxial movement of the bone fastener 950. The clamp portion 1032 may have an outer surface, for example, with a plurality or protrusions and recesses, a threaded portion, or other texture. The clamp portion 1032 may also include at least one slit 1038 extending therethrough to allow the clamp portion 1032 to be compressed around the head 952 of the fastener 950, for example, when the snap ring 1034 tightens around the base of the clamp portion 1032. The slit 1038 may extend from a top portion to a bottom portion of the clamp portion 1032 or along a length thereof and may extend completely or partially therethrough. The slit 1038 may be linear or non-linear in shape. The configuration and number of slits 1038 may be selected to obtain the desired amount of compression on the head 952 of the fastener 950 when the ring portion 1034 compresses the clamp portion 1032.

According to a method, the connector 1000 may be used to extend an existing fusion construct. For example, the posterior aspects of the spine may be exposed or accessed via a minimally invasive surgical (MIS) approach. The coupling element 1002 may be positioned onto an existing bone fastener 950, which was previously secured into the pedicle of a first vertebra. A tulip including a second bone fastener 950 may be inserted into the pedicle of a second, adjacent vertebra and the tulip may be attached to the rod portion 1010 of the connector 1000. Once the final positioning has been obtained, the locking set screw 1036 may be tightened to achieve the final construct.

Figure 16A:
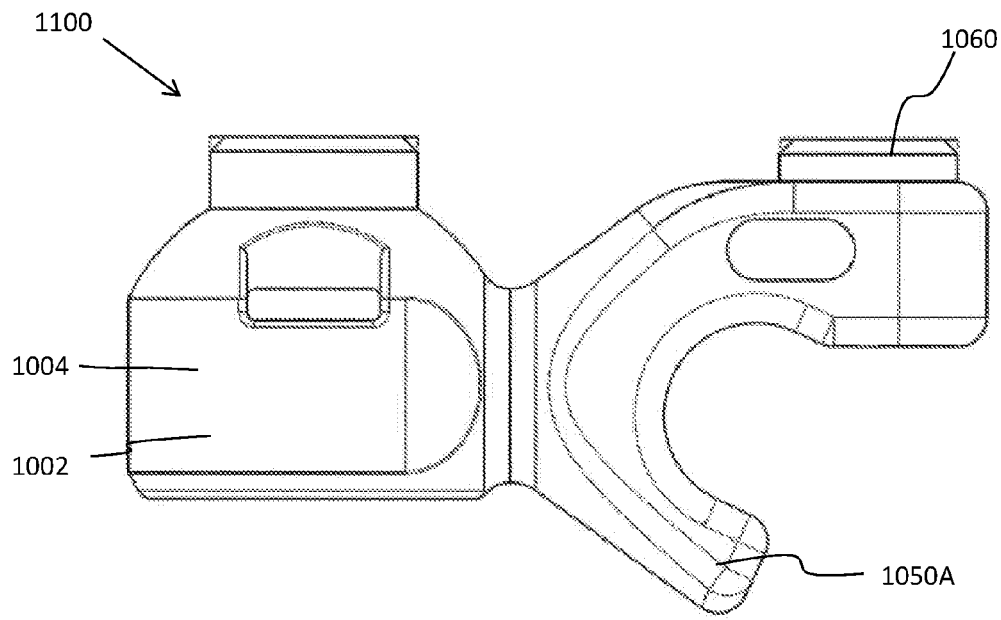
FIG. 16A is a side view of the an open offset connector member in accordance with another embodiment.
Figure 16B:
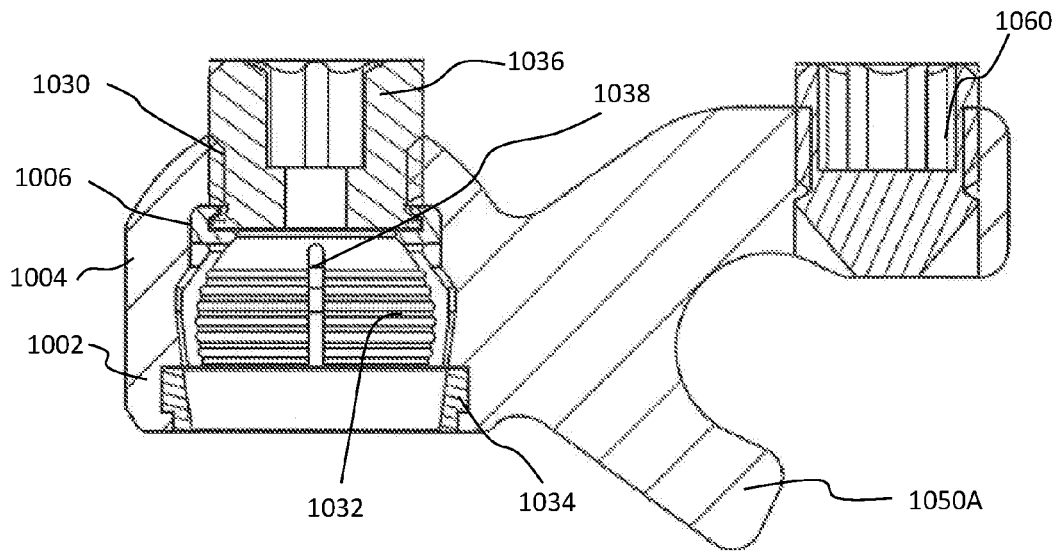
FIG. 16B is a cross-sectional view of the open offset connector member of FIG. 16A.

FIGS. 16A-16B illustrate an open offset connector or implant 1100 which may be utilized as part of a stabilization system. The coupling element 1002 and locking assembly 1030 are substantially the same as that disclosed for the connector 1000 in FIGS. 15A-15C. Instead of the integral rod, implant 1100 includes a connector or coupling element 1002 with an integral rod receiving channel or engagement portion 1050A. The rod receiving channel or engagement portion 1050A is configured to receive a fixation element, such as an elongate rod 960. Open offset connector 1000 may be offered in both modular and preassembled configurations allowing for an extremely low profile iliac fixation point, which is particularly advantageous for surgical procedures performed on small stature patients.

Implant 1100 includes engagement portion 1050A for receiving a fixation element, such as an elongate rod 960, and a second locking set screw 1060 for securing the received fixation element therein. The engagement portion 1050A may include a c-shaped channel or opening configured to mimic at least a portion of the outer configuration of the elongate rod 960. The second set screw 1060 may be received in an opening of the implant 1100 positioned above and in fluid communication with the c-shaped channel. The base of the second set screw 1060 may include one or more tapered or angled portions such that when the set screw 1060 is lowered into the c-shaped channel, the base of the second set screw 1060 contacts an upper or side surface of the elongate rod 960, thereby securing the rod 960 in the implant 1100. Similar to connector member 400A shown in FIGS. 7A-7B, the elongate rod 960 may be advantageously received in a preliminary snap-fit or interference connection at engagement portion 1050A. Second locking set screw 1060 may be provided to lock or clamp the elongate rod 960 within the engagement portion 1050A as screw 1060 is rotated or advanced into connector 1100.

Figure 17A:
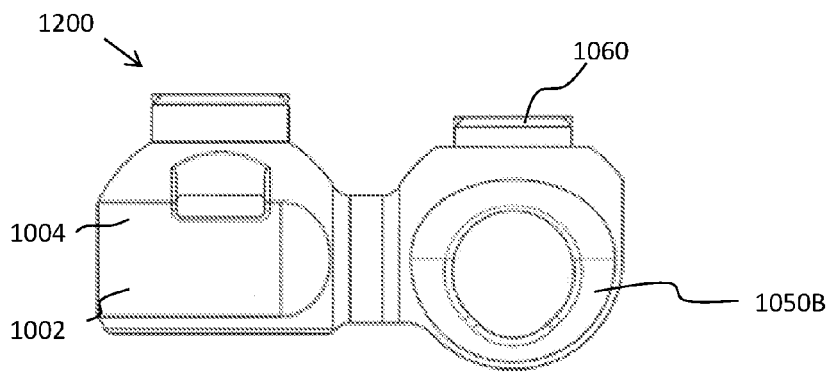
FIG. 17A is a side view of a closed offset connector member in accordance with another embodiment.
Figure 17B:
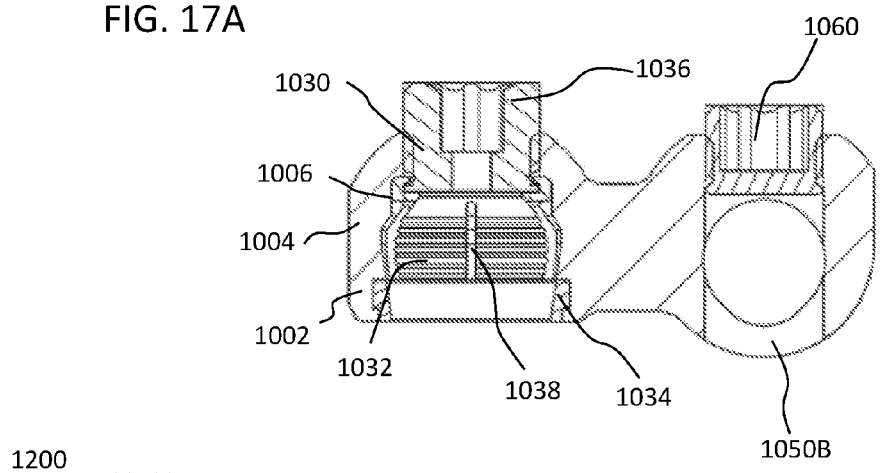
FIG. 17B is a cross-sectional view of the closed offset connector member of FIG. 17A.
Figure 17C:
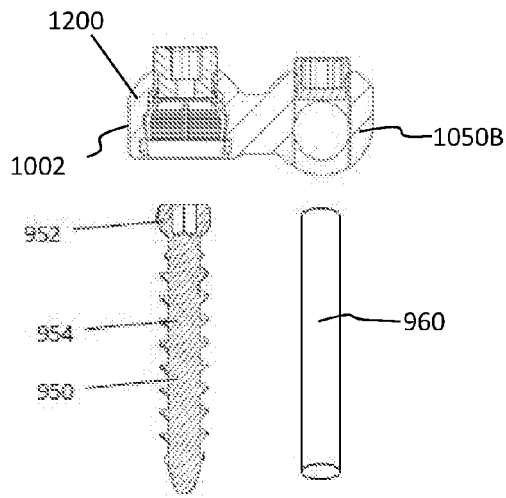
FIG. 17C is an exploded view of the closed offset connector member of FIG. 17A with a bone fastener and elongate bone fixation element.

FIGS. 17A-17C illustrate a closed offset connector 1200 which may be utilized as part of a stabilization system. The coupling element 1002 and locking assembly 1030 are substantially the same as that disclosed for the connector 1000 in FIGS. 15A-15C. Instead of the integral rod, implant 1200 includes a connector or coupling element 1002 with an integral closed rod receiving opening or engagement portion 1050B. The closed rod receiving opening or engagement portion 1050B is configured to receive a fixation element, such as an elongate rod 960.

Unlike engagement portion 1050A, engagement portion 1050B is closed to fully enclose a received spinal fixation element, such as an elongate rod 960. Thus, the engagement portion 1050A may completely encircle the elongate rod 960. The closed opening in the engagement portion 1050A may be substantially cylindrical, oval, or otherwise complementary to the shape of the rod 960. The second locking set screw 1060 advances through an opening in the top portion of the implant 1200, which is in fluid communication with the closed opening, to engage an upper surface of the rod 960, thereby securing the rod 960 therein. The second locking set screw 1060 may be similar to locking set screw 1036, however, it should be appreciated that different locking assemblies and/or set screws for establishing bone fixation, such as iliac fixation points, may be utilized. Closed offset connector 1200 may also be offered in both modular and preassembled configurations allowing for extremely low profile fixation points.

Figure 18A:
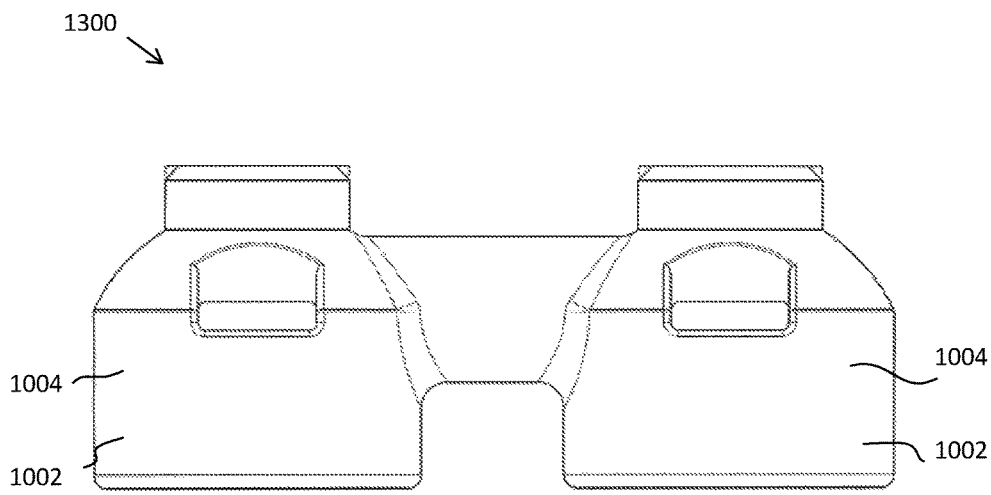
FIG. 18A is a side perspective view of a one-level connector in accordance with another embodiment.
Figure 18B:
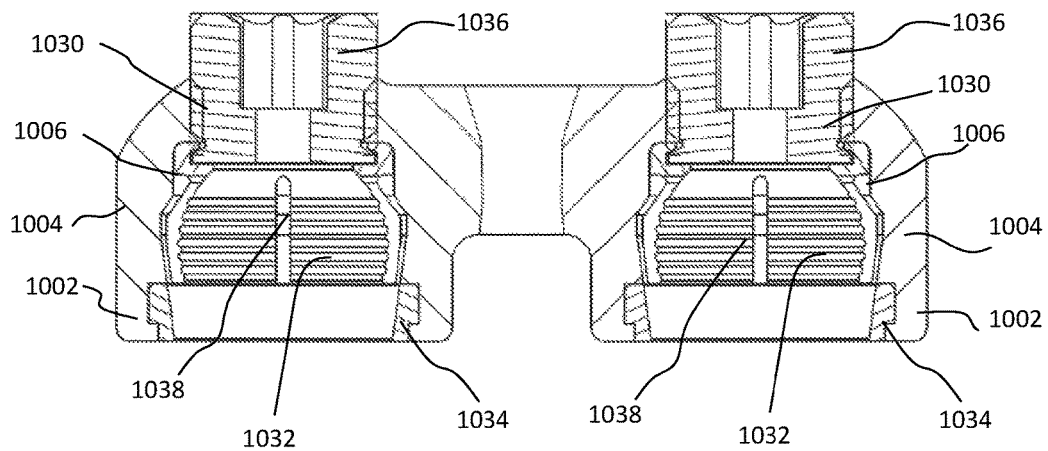
FIG. 18B is a cross-sectional view of the one level connector of FIG. 18A.

FIGS. 18A-18B illustrate a one level connector 1300 which may be utilized as part of a stabilization system.

Instead of the integral rod, implant 1300 includes a first connector or coupling element 1002 with an integral, second connector or coupling element 1002. The coupling elements 1002 and locking assemblies 1030 are substantially the same as that disclosed for the connector 1000 in FIGS. 15A-15C. One-level connector 1300 includes first and second coupling elements 1002 and first and second locking assemblies 1030 associated with the first and second coupling elements 1002. The first and second coupling elements 1002 may be separated a distance from one another, for example, by a rod portion, interconnecting the two adjacent coupling elements 1002. One level connector 1300 may be offered in both modular and preassembled configurations and allows for extremely low profile fixation points, for example in sacral fixation points, which is useful for small statute patients.

All references cited herein are expressly incorporated by reference in their entirety. There are many different features to the present invention and it is contemplated that these features may be used together or separately. Thus, the features of one embodiment may be used in another embodiment. Unless mention was made above to the contrary, it should be noted that all of the accompanying drawings are not to scale. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. A coupling device comprising:
   a bone fastener having a head portion;
   a coupling element having a body portion for receiving the bone fastener and an extension portion extending transversely from the body portion; and
   a locking assembly received in the coupling element, the locking assembly including a locking member, a clamp portion, and a ring portion, wherein the locking member is configured to contact an upper portion of the clamp portion and the ring portion is configured to at least partially surround a lower portion of the clamp portion, wherein the clamp portion is configured to engage a portion of the head portion of the bone fastener, and wherein the ring portion is configured to engage a portion of the head portion of the bone fastener,
   wherein, when unlocked, the bone fastener is moveable with respect to the clamp portion to allow for polyaxial movement of bone fastener relative to the coupling element, and when locked, the bone fastener is fixed relative to the coupling element,
   wherein the clamp portion includes at least one slit extending therethrough to allow the clamp portion to be compressed around the head portion of the bone fastener when the locking assembly is locked, and wherein the at least one slit extends through the lower portion of the clamp portion and toward the upper portion of the clamp portion without extending through an upper surface of the clamp portion, and
   wherein an upper portion of the ring portion comprises an annular collar extending radially outward.

2. The device of claim 1, wherein the extension portion is in the form of an elongate rod terminating at a free end.

3. The device of claim 1, wherein the extension portion is in the form of an engagement portion having an open rod receiving channel configured to receive an elongate rod.

4. The device of claim 3, wherein the open rod receiving channel is a c-shaped channel configured to receive the elongate rod, and the elongate rod is secured in the c-shaped channel by a second locking member.

5. The device of claim 1, wherein the extension portion is in the form of an engagement portion having a closed rod receiving channel configured to receive an elongate rod.

6. The device of claim 5, wherein the closed rod receiving channel is a substantially cylindrical shaped opening configured to receive the elongate rod, and the elongate rod is secured in the cylindrical shaped opening by a second locking member.

7. The device of claim 1, further comprising a second coupling element having a second body portion and a second locking assembly connected to the extension portion of the coupling element.

8. The device of claim 7, wherein the second locking assembly includes a second locking member, a second clamp portion, and a second ring portion, wherein the second locking member is configured to contact an upper portion of the second clamp portion and the second ring portion is configured to at least partially surround a lower portion of the second clamp portion.

9. The device of claim 1, wherein the locking member is in the form of a set screw configured to apply a downward force on the clamp portion and cause the ring portion to clamp around the clamp portion, thereby locking the bone fastener therein.

10. The assembly of claim 1, wherein the at least one slit is non-linear in shape.

11. A coupling assembly comprising:
    a first bone fastener having a head and a shaft extending therefrom, the shaft configured to engage a first vertebra;
    a first coupling element having a first body portion housing a first locking assembly and an extension portion extending transversely from the first body portion, the first locking assembly comprising a first rotatable locking member, a first clamp portion, and a first ring portion configured to at least partially surround only a lower portion of the first clamp portion, and the head of the first bone fastener is received in the first clamp portion; and
    wherein, when unlocked, the first bone fastener is moveable in the first clamp portion to allow for polyaxial movement of the first bone fastener relative to the first clamp portion, and when locked, the position of the first bone fastener is fixed relative to the first coupling element,
    wherein the first clamp portion includes at least one slit extending therethrough to allow the first clamp portion to be compressed around the head of the first bone fastener when the first locking assembly is locked, and wherein the at least one slit extends through the lower portion of the first clamp portion and toward an upper portion of the first clamp portion without extending through an upper surface of the first clamp portion, and
    wherein an upper portion of the first ring portion comprises an annular collar extending radially outward.

12. The assembly of claim 11, wherein the extension portion is in the form of an elongate rod terminating at a free end.

13. The assembly of claim 11, wherein the extension portion is in the form of an engagement portion having an open rod receiving channel configured to receive an elongate rod.

14. The assembly of claim 13, wherein the open rod receiving channel is a c-shaped channel configured to receive the elongate rod, and the elongate rod is secured in the c-shaped channel by a second locking member.

15. The assembly of claim 11, wherein the extension portion is in the form of an engagement portion having a closed rod receiving channel configured to receive an elongate rod.

16. The assembly of claim 15, wherein the closed rod receiving channel is a substantially cylindrical shaped opening configured to receive the elongate rod, and the elongate rod is secured in the cylindrical shaped opening by a second locking member.

17. The assembly of claim 11, further comprising a second coupling element having a second body portion and a second locking assembly connected to the extension portion of the first coupling element.

18. The assembly of claim 17, wherein the second locking assembly includes a second locking member, a second clamp portion, and a second ring portion, wherein the second locking member is configured to contact an upper portion of the second clamp portion and the second ring portion is configured to at least partially surround a lower portion of the second clamp portion.

19. The assembly of claim 11, wherein the first locking member is in the form of a set screw configured to apply a downward force on the first clamp portion and cause the first ring portion to clamp around the first clamp portion, thereby locking the first bone fastener therein.

* * * * *